US010238756B2

United States Patent
Ho et al.

(10) Patent No.: US 10,238,756 B2
(45) Date of Patent: Mar. 26, 2019

(54) LIPID NANOPARTICLES AND USES THEREOF

(71) Applicant: Tongli Biomedical Co., Ltd., Suzhou (CN)

(72) Inventors: Rodney J. Y. Ho, Mercer Island, WA (US); John C. Kraft, II, Seattle, WA (US); Mingxin Qian, Suzhou (CN)

(73) Assignee: Tongli Biomedical Co., Ltd., Suzhou (CN)

( * ) Notice: Subject to any disclaimer, the term of this patent is extended or adjusted under 35 U.S.C. 154(b) by 35 days.

(21) Appl. No.: 14/725,178

(22) Filed: May 29, 2015

(65) Prior Publication Data

US 2016/0228579 A1    Aug. 11, 2016

Related U.S. Application Data

(60) Provisional application No. 62/113,480, filed on Feb. 8, 2015.

(30) Foreign Application Priority Data

Apr. 7, 2015 (CN) .......................... 2015 1 0160468

(51) Int. Cl.
*A61K 49/00* (2006.01)
(52) U.S. Cl.
CPC ...... *A61K 49/0052* (2013.01); *A61K 49/0034* (2013.01); *A61K 49/0082* (2013.01)
(58) Field of Classification Search
CPC ............ A61K 49/0052; A61K 49/0082; A61K 49/0034
See application file for complete search history.

(56) References Cited

U.S. PATENT DOCUMENTS

2014/0369935 A1* 12/2014 Okamoto ........... A61K 41/0057 424/9.6
2016/0106869 A1*  4/2016 Ghiani ............... A61K 49/0078 424/9.6

OTHER PUBLICATIONS

Nguyen et al. Fluorescence-guided surgery with live molecular navigation—a new cutting edge. Nat Rev Cancer. 2013;13(9):653-62.
Baker K. Binding of Sulfobromophthalein (BSP) Sodium and IndocyanineGreen (ICG) by Plasma alpha 1 Lipoproteins. Proc Soc Exp Biol Med. Aug.-Sep. 1966;122(4):957-63.
Mordon S. et al. Indocyanine green: physicochemical factors affecting its fluorescence in vivo. Microvasc Res. 1998;55(2):146-52.
Saxena V. et al. Degradation kinetics of indocyanine green in aqueous solution. J Pharm Sci. 2003;92(10):2090-7.
Zhou et al. Aggregation and degradation of indocyanine green. Proc. SPIE. 1994;2128:495.
Kraft JC et al. Emerging research and clinical development trends of liposome and lipid nanoparticle drug delivery systems. J Pharm Sci. 2014;103(1):29-52.
Daemen T et al. Different intrahepatic distribution of phosphatidylglycerol and phosphatidylserine liposomes in the rat. Hepatology. 1997;26(2):416-23.
Jeong HS et al. The effect of mannosylation of liposome-encapsulated indocyanine green on imaging of sentinel lymph node. J Liposome Res. 2013;23(4):291-7.
Proulx ST, et al. Quantitative imaging of lymphatic function with liposomal indocyanine green. Cancer Res. 2010;70(18)1053-62.
Turner DC, et al. Near-infrared image-guided delivery and controlled release using optimized thermosensitive liposomes. Pharm Res. 2012;29(8):2092-103.
Zhuang Y, et al. PEGylated cationic liposomes robustly augment vaccine-induced immune responses: Role of lymphatic trafficking and biodistribution. J Control Release. 2012;159(1):135-42.
Suganami A, et al. Preparation and characterization of phospholipid-conjugated indocyanine green as a near-infrared probe. Bioorg Med Chem Lett. 2012;22(24):7481-5.
Kraft JC, et al. Interactions of indocyanine green and lipid in enhancing near-infrared fluorescence properties: the basis for near-infrared imaging in vivo. Biochemistry. 2014;53(8):1275-83.
Hua J, et al. In vivo imaging of choroidal angiogenesis using fluorescence-labeled cationic liposomes. Mol Vis. 2012;18:1045-54.
Li X., et al. Tumor localization using fluorescence of indocyanine green (ICG) in rat models, Proc. SPIE 2389, Optical Tomography, Photon Migration, and Spectroscopy of Tissue and Model Media: Theory, Human Studies, and Instrumentation, 789 (1995).
Philip R., et al. Absorption and fluorescence spectroscopic investigation of indocyanine green. J Photochem Photobiol A Chem. (1996) 96;1-3:137-148.
Rajagopalan R., et al. Stabilization of the Optical Tracer Agent Indocyanine Green Using Noncovalent Interactions. J Photochem Photobiol A Chem. (2000) 71;3:347-350.
Engel E, et al. Light-induced decomposition of indocyanine green. Invest Ophthalmol Vis Sci. 2008;49(5):1777-83.
Holzer W., et al. Photostability and thermal stability of indocyanine gree. J. Photochem. Photobiol. B: Biol. 47 (1998) 155-164.
Sandanaraj BS, et al. Fluorescent nanoprobes as a biomarker for increased vascular permeability: implications in diagnosis and treatment of cancer and inflammation. Bioconjug Chem. 2010;21(1):93-101.
Proulx ST, et al. Use of a PEG-conjugated bright near-infrared dye for functional imaging of rerouting of tumor lymphatic drainage after sentinel lymph node metastasis. Biomaterials. 2013;34(21):5128-37.
Macdonald RI. Characteristics of self-quenching of the fluorescence of lipid-conjugated rhodamine in membranes. J Biol Chem. 1990;265(23):13533-9.

\* cited by examiner

*Primary Examiner* — Robert S Cabral
(74) *Attorney, Agent, or Firm* — K&L Gates LLP; Louis C. Cullman; Hal Gibson

(57) ABSTRACT

The present invention relates to lipid-associated indocyanine green particles for enhanced functional high-resolution near-infrared fluorescence medical imaging of lymphatic vessels, lymph nodes, lymphatic abnormalities, tumors, and inflammation.

19 Claims, 20 Drawing Sheets

LIPID NANOPARTICLES AND USES THEREOF

CROSS REFERENCE TO RELATED APPLICATIONS

This application claims the benefit of, and priority to, U.S. Provisional Patent Application Ser. No. 62/113,480, filed Feb. 8, 2015, and Chinese Patent Application Serial No. 201510160468.1, filed Apr. 7, 2015, the entire disclosures of which are hereby incorporated by reference in their entireties.

STATEMENT REGARDING FEDERALLY SPONSORED RESEARCH OR DEVELOPMENT

This invention was made with U.S. Government support under Grant Nos. AI077390, RR00166, RR025014 awarded by the National Institutes of Health. The U.S. government has certain rights in the invention.

FIELD OF THE INVENTION

The present invention relates to preparation and use of lipid nanoparticles comprising dyes such as indocyanine green for enhanced near-infrared fluorescence image intensity, resolution, and delineation of abnormal or abnormal tissues and cells in the body.

BACKGROUND OF THE INVENTION

For effective treatment and diagnosis of disease, it is advantageous to be able to image affected organs. There are many widely used types of imaging; however, these techniques do not have the versatility or contrast to look at the vasculature or the lymphatic system. An emerging technology to study these systems is an optical imaging technique referred to as near-infrared fluorescence (NIRF) imaging (~700-900 nm), which has excellent safety because it does not involve ionizing radiation, has minimal interference from blood and tissue autofluorescence (~500-600 nm) (i.e., background signal/fluorescence), and is non-invasive. The fluorescence imaging method involves irradiating fluorescent dye with light and detecting fluorescence emitted from the dye, and is widely used in various types of biological imaging. This method is used in angiography and can be used for intraoperative assessment of vessel function and/or metastasis. Unlike other techniques, NIRF imaging also has the capability to image lymphatic systems, giving important information to clinicians about lymphatic architecture and function in a patient. Nevertheless, NIRF imaging faces challenges due to its inability to image deep tissue (can only image ~1 cm into the body because of light scattering).

ICG is a clinically used dye in NIRF imaging (with an 820 nm emission) and is the only NIRF molecule approved by the US Food and Drug Administration (FDA) and European Medicines Agency (EMA) for human use. ICG is indicated for determining cardiac output, hepatic function and liver blood flow, and for ophthalmic angiography. ICG is used off-label or in research to visualize fluid-filled anatomical structures (for example, blood, cerebrospinal fluid, lymph, or urine) or as a contrast agent for vascular, renal, or excretory pathways (1). In aqueous environments, ICG molecules aggregate and ICG fluorescence readily degrades (reducing the overall fluorescence intensity) (2-5). In blood, ICG binds to plasma proteins, partially and temporary improving its fluorescence intensity, but eventually dissociates and becomes subjected to degradation in aqueous fluid. In vivo ICG fluorescence intensity and duration may vary with fluctuating plasma protein and lipoprotein concentrations and interindividual variation.

Recent reports on ICG and liposomes with diverse physiochemical characteristics describe resource-intensive preparation procedures (≥4 steps) to encapsulate ICG in liposomes (8-12). However, these liposomes with varying compositions were prepared without a full understanding of the interactions between ICG and lipids. Under certain conditions, when ICG is encapsulated in the aqueous compartment of liposomes it can by default partially and physically interact with phospholipids in the liposome membrane. The lipid-ICG binding under these methods and compositions involves incomplete and unstable interactions. These formulations are not intended to intercalate or embed ICG in lipids. The results vary in the stability and quantum yield of ICG as well as in its use as an imaging product. Also, only a fraction of ICG may be encapsulated in the aqueous compartment of liposomes, thus requiring removal of the free ICG from the preparation procedure—a step that increases the potential of contamination and adds cost due to wastage and separation procedures.

There is need for improved ICG delivery systems.

SUMMARY OF THE INVENTION

In one aspect, the present invention provides a composition, comprising: (i) a lipid nanoparticle comprising a lipid membrane and an aqueous core; and (ii) a plurality of indocyanine green (ICG), wherein one or more of the ICG is embedded in the lipid membrane.

In some embodiments, the lipid molecules comprise 1,2-Distearoyl-sn-glycero-3-phosphocholine (DSPC), and 1,2-distearoyl-sn-glycero-3-phosphoethanolamine-N-methoxy-polyethylene glycol-2000 (DSPEmPEG2000).

In some embodiments, at least about 95% of the ICG is embedded in the lipid membrane. In some embodiments, at least about 99% of the ICG is embedded in the lipid membrane. In some embodiments, about substantially 100% of the ICG is embedded in the lipid membrane.

In some embodiments, there is less than 5% of the ICG is encapsulated in the aqueous core. In some embodiments, there is less than 1% of the ICG is encapsulated in the aqueous core. In some embodiments, there is no detectable amount of the ICG is encapsulated in the aqueous core.

In some embodiments, the lipid nanoparticle is suspended in a salt composition comprising a biocompatible buffer, such as one has a pH 5-8 and Osm ~303 mOSM. Examples of such buffer include normal saline, Ringer's, dextrose 5% in water, or a buffer of 0.9% NaCl and about 20 mM NaHCO3.

In some embodiments, the nanoparticle has an average size of 50 nm to 100 nm.

In some embodiments, the nanoparticle has a negative surface charge.

In some embodiments, the nanoparticle is stable in serum with between about 90%, to about 100% of its initial fluorescence retained in heat-inactivated rat serum after 6 h, at 25° C.

In some embodiments, the nanoparticle has fluorescence intensity between 4- and 5-fold higher than that of free ICG in aqueous solution.

In some embodiments, the nanoparticle has a fluorescence intensity between 4- and 100,000-fold higher than that of free ICG in aqueous solution after being stored at 4° C. for between 0 and 300 days.

In some embodiments, the composition is potent at less than about 0.5 mg/kg ICG dose. In some embodiments, the composition is potent at about 0.05 mg/kg ICG dose.

In another aspect, the present invention provides a kit, comprising the composition/LNP provided herein and optionally an instruction of how to use the kit.

In yet another aspect, the present invention provides a method for imaging a tissue or organ in a subject, comprising: administering to a subject in need of imaging a suitable amount of the composition provided herein, and obtain an image of a tissue or organ of the subject.

In some embodiments, the amount of the composition equals to between about 0.05 mg/kg to about 0.5 mg/kg ICG dose.

In some embodiments, the tissue or organ is selected from the group consisting of: Lymphatic vessels, Secondary lymphoid tissues, Blood vessels, Endothelial lesions such as atherosclerosis, Cancer/tumors, Tertiary lymphoid tissues such as at the sites of inflammation, Liver, Bile duct, Gall bladder, and Intestine In a further aspect, the present invention provides a method for preparation of nanoparticles, comprising: (a) mixing an indocyanine green (ICG) and lipid molecules together in an organic solvent; (b) evaporating the organic solvent to create a thin film comprising the lipid molecules and the ICG; and (c) hydrating the thin film with a buffered salt and particle size reduction.

In some embodiments, the lipid molecules comprise 1,2-Distearoyl-sn-glycero-3-phosphocholine (DSPC), and 1,2-distearoyl-sn-glycero-3-phosphoethanolamine-N-methoxy-polyethylene glycol-2000 (DSPEmPEG2000).

In some embodiments, the organic solvent comprises ethanol, methanol, chloroform, ethyl acetate, or DMSO.

In some embodiments, the buffered salt comprises about 0.9% NaCl and about 20 mM $NaHCO_3$.

In some embodiments, the method does not comprise a filtration step, a purification step, or a separation step, or a combination thereof.

In a further aspect, the present invention provides an indocyanine green-containing particle, comprising: an indocyanine green; and a particle comprising a lipid membrane and an aqueous core, wherein the indocyanine green is embedded in the lipid membrane.

In some embodiments, substantially 100% of the indocyanine green is embedded in the lipid membrane. In some embodiments, there is no detectable amount of the indocyanine green in the aqueous core.

In another aspect, the present invention provides a contrast agent for photoimaging, comprising: the indocyanine green-containing particle provided herein and a dispersion medium for dispersing the indocyanine green-containing particle.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

INCORPORATION BY REFERENCE

Figure 1:
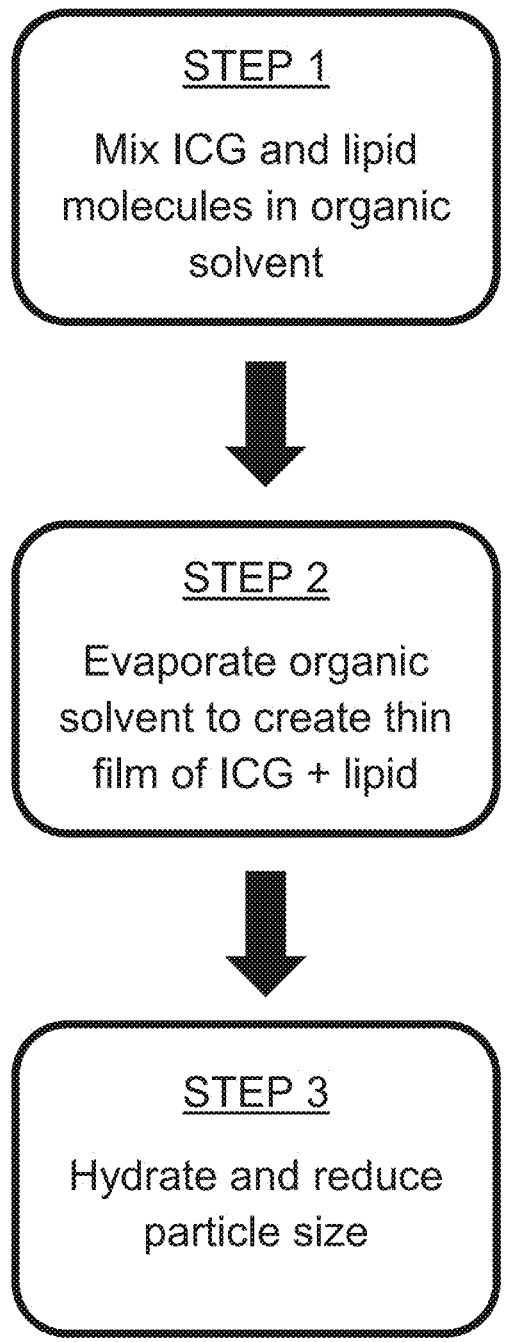
FIG. 1 depicts one exemplary schematic of 3-step preparation procedure.

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well-known and commonly employed in the art. Standard techniques are used for nucleic acid and peptide synthesis. The techniques and procedures are generally performed according to conventional methods in the art and various general references, which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

I. The Compositions

The present invention relates to compositions and use of biomedical imaging, and more particularly to the unique preparation methods, composition, and infrared fluorescence emitting particles in nanometer diameters for near-infrared fluorescence (NIRF) medical imaging including blood, tissues, and the lymphatic vasculature and lymph nodes (LNs).

In one aspect, the present invention provides composition, comprising: (i) a lipid nanoparticle (e.g, a sphere) comprising a lipid membrane and an aqueous core; and (ii) a plurality of indocyanine green (ICG), wherein one or more of the ICG is embedded in the lipid membrane of the nanoparticle.

A. Lipid Nanoparticles

In general, the composition provided herein comprises a nanoparticle.

The size of the nanoparticles of the present invention may range between about 20 nm-20 microns, for example from about 20 nm-5 microns, about 80 nm-2 microns, about 80 nm-1 micron. Thus, although referred to herein as "nanoparticles", micron scale particles are also encompassed. For intravenous or intra-arterial injection administration, the size of the particles is preferably in the range of about 80 nm-100 nm. For other routes of administration, for example transnasal, larger particles may be used. In some embodiments, particles with a size in the range of about 20-300 nm, for example about 20-100 nm, 20-50 nm are used. Each possibility represents a separate embodiment of the invention.

In some embodiments, the particle size of the particle is not particularly limited, provided that when the particle is used as a contrast agent, in particular, a contrast agent for a lymph node, setting its hydrodynamic mean particle size to 1,000 nm or less can enhance the ease with which the particle is taken in a lymph duct or a tissue (tissue permeability) and its retentivity in a lymph node or the tissue.

When the particle size is 1,000 nm or less, a larger amount of particles can be accumulated in a tumor site than that in a normal site in a living organism by an enhanced permeability and retention (EPR) effect. The tumor site can be specifically imaged by detecting the accumulated particles with various image-forming modalities such as fluorescence and photoacoustics. In addition, when the particle size exceeds 1,000 nm, efficient intake in a tissue such as a lymph duct cannot be expected. Consequently, the mean particle size is preferably set to 10 nm or more and 1,000 nm or less. The mean particle size is more preferably 20 nm or more and 500 nm or less, still more preferably 20 nm or more and 200 nm or less, particularly preferably 20 to 100 nm. This is because when the particle size of the particle is 200 nm or less, the particle is hardly taken in a macrophage in blood and hence its retentivity in the blood may improve.

The particle size can be measured through observation with an electron microscope or by a particle size-measuring method based on a dynamic light scattering method. When the particle size is measured based on the dynamic light scattering method, a hydrodynamic diameter is measured with a dynamic light scattering analyzer (PSS-NICOMP 380 ZLS instrument manufactured by Particle Sizing Systems, Port Richey, Fla.) by the dynamic light scattering (DLS) method.

As used herein, the term "about", when referring to a measurable value such as an amount or size, is meant to encompass variations of +/−10%, more preferably +1-5%, even more preferably +/−1%, and still more preferably +/−0.1% from the specified value, as such variations are appropriate to achieve the intended purpose.

As used herein, the "size" of the nanoparticles indicates that the longest dimension of the nanoparticles (width, length or diameter) is in the specified range. Typically, the average particle size in a preparation comprising the nanoparticles is in the specified range. The nanoparticles may be of a uniform shape, e.g., spherical or elongated, or may have a variety of shapes. Preferably, the nanoparticle here is spheric.

In some embodiments, the nanoparticle has an average size of 50 nm to 100 nm, preferably from 50 nm to 80 nm.

In general, the nanoparticles in the composition (such as a pharmaceutical composition) provided herein has a uniformity of about 50±5 nm, about 55±5 nm, about 60±5 nm, about 65±5 nm, about 70±5 nm, about 75±5 nm, about 80±5 nm, about 85±5 nm, about 90±5 nm, about 95±5 nm, or about 100±5 nm. In some embodiments, the LNPs have a uniformity of 1 nm, ±2 nm, ±3 nm, ±4 nm, or ±5 nm.

The nanoparticles of the present invention may be negatively or positively charged. As used herein, the "charge" of the nanoparticles refers to their surface charge, known as zeta potential. For intravenous or intraarterial administration, negatively charged particles are currently preferred. The range of surface charge (zeta potential) for negatively charged particles may range from about −20 to −55 mV.

Particle size and zeta-potential measurements can be performed by methods known in the art, for example, by dynamic light scattering (DLS) using commercially available instruments, e.g. a Zetasizer NanoZS (Malvern, UK).

In some embodiments, the nanoparticle has a negative surface charge of between about −5 to −100 mV.

In some embodiments, the nanoparticles of the present invention are liposomes.

Lipid particles for use in this invention may be prepared to include liposome-forming lipids and phospholipids, and membrane active sterols (e.g. cholesterol). Liposomes may include other lipids and phospholipids which are not liposome forming lipids.

Phospholipids may be selected, for example, from a lecithin (such as egg or soybean lecithin); a phosphatidylcholine (such as egg phosphatidylcholine); a hydrogenated phosphotidylcholine; a lysophosphatidyl choline; dipalmitoylphosphatidylcholine; distearoyl phosphatidylcholine; dimyristoyl phosphatidylcholine; dilauroylphosphatidylcholine; a glycerophospholipid (such as phosphatidylglycerol, phosphatidylserine, phosphatidylethanolamine, lysophosphatidylethanolamine, phosphatidylinositol, phosphatidylinositol phosphate, phosphatidylinositol bisphosphate and phosphatidylinositol triphosphate); sphingomyelin; cardiolipin; a phosphatidic acid; a plasmalogen; or a mixture thereof. Each possibility represents a separate embodiment of the invention.

Examples of other lipids that can be used include a glycolipid (such as a glyceroglycolipid, e.g. a galactolipid and a sulfolipid, a glycosphingolipid, e.g., a cerebroside, a glucocerebroside and a galactocerebroside, and a glycosylphosphatidylinositol); a phosphosphingolipid (such as a ceramide phosphorylcholine, a ceramide phosphorylethanolamine and a ceramide phosphorylglycerol); or a mixture thereof. Each possibility represents a separate embodiment of the invention.

Negatively or positively charged lipid nanoparticles can be obtained, for example, by using anionic or cationic phospholipids or lipids. Such anionic/cationic phospholipids or lipids typically have a lipophilic moiety, such as a sterol, an acyl or diacyl chain, and where the lipid has an overall net negative/positive charge.

The above described lipids and phospholipids can be obtained commercially or prepared according to published methods in the art.

Lipid particles can be prepared by methods known in the art, reviewed, for example, in Scholar et al., 2012, International Journal of Pharmaceutical Studies and Research, 3(2): 14-20; Akbarzadeh et al., 2013, Nanoscale Research Letters, 8:102. Exemplary procedures are described hereinbelow. Extrusion of liposomes through a small-pore membrane, e.g. polycarbonate membrane, is an effective method for reducing size down to a relatively well-defined size distribution. Typically, the suspension is cycled through the membrane several times (using membranes of decreasing pore sizes) until the desired liposome size distribution is achieved. The lipid particles extrusion through successively smaller-pore membranes, enables a gradual reduction in liposome size down to the desired size. The down-sized processed lipid particle suspension may be readily sterilized by passage through a sterilizing membrane having a particle discrimination size of, e.g., about 0.2 microns, such as a conventional 0.22 micron depth membrane filter. If desired, the liposome suspension can be lyophilized in the presence of a suitable cryoprotectant for storage and reconstituted by hydration shortly before use.

In general, the lipid nanoparticle of the present invention are prepared by mixing the dyes such as ICG with the lipid molecules before generating the particles, as described in more detail herein.

In some embodiments, the lipid molecules forming the nanoparticle comprise two phospholipid species, 1,2-Distearoyl-sn-glycero-3-phosphocholine (DSPC), and 1,2-distearoyl-sn-glycero-3-phosphoethanolamine-N-methoxy-polyethylene glycol-2000 (DSPEmPEG2000).

B. Fluorescent Dyes

In some embodiments, the nanoparticles of the present invention comprise at least one near-infrared (NIR) fluorescent dye (or probe) embedded in the lipid.

In some embodiments, the binding is non-covalent.

By "near-infrared (NIR) fluorescent dye" or "near-infrared (NIR) fluorescent probe" herein is meant as a molecule or entity suitable for imaging applications, capable of absorbing and emitting light in the NIR spectral range. In particular, it is a fluorescent entity having an excitation light and emission light in the NIR spectral range, preferably in the range of about 700 to 900 nm. NIR radiation is typically defined as having a wavelength in the range of about 700 nm-1400 nm. NIR fluorescent probes of the present invention are preferably those that absorb and emit NIR light in the range of about 700 to 900 nm, which is considered a biological "NIR window".

Examples of suitable NIR fluorescent probes include dyes, e.g. cyanine dyes, such as indocyanine green (ICG), Cy5, Cy5.5, Cy5.18, Cy7 and Cy7.5; an IRDYE®, an ALEXA FLUOR® dye, a BODIPY® dye, an ANGIOS TAMP™ dye, a SENTIDYE™ dye, XENOLIGHT DIR™ fluorescent dye, VIVOTRACK™ NIR fluorescent imaging agent, KODAK X-SIGHT™ dyes and conjugates, DYLIGHT™ dyes. NIR quantum dots may also be utilized as probes (synthesis and functionalization of NIR quantum dots is described, for example, in Ma et al., 2010, Analyst, 135:1867-1877). Each possibility represents a separate embodiment of the invention. Other dyes include Methylene Blue, ProSense, and MMPSense. Figueiredo, J. L., Alencar, H., Weissleder, R. & Mahmood, U. Near infrared thoracoscopy of tumoral protease activity for improved detection of peripheral lung cancer. Int. J. Cancer 118, 2672-2677 (2006), and Nguyen, Q. T., and Tsien, R. Y. (2013) Fluorescence-guided surgery with live molecular navigation: A new cutting edge. Nat. Rev. 13, 653-662.

In some embodiments, the fluorescent dye is a lipophilic (Log P>2) fluorescent dyes with molecular weight between 300-1500 g/mol, such as indocyanine green, ethylene Blue. ProSense, and MMPSense.

Table 6 lists additional NIR dyes that may be embedded into the lipid nanoparticles of the present invention. Any hydrophobic small molecule that fluoresces may be embedded in our lipid nanoparticles.

TABLE 6

List of near-infrared fluorescent dyes.

| Near-infrared Dye | Absorption Max (nm) | Emission Max (nm) |
|---|---|---|
| Alexa Fluor 660 | 663 | 690 |
| Alexa Fluor 680 | 679 | 702 |

TABLE 6-continued

List of near-infrared fluorescent dyes.

| Near-infrared Dye | Absorption Max (nm) | Emission Max (nm) |
|---|---|---|
| Alexa Fluor 700 | 702 | 723 |
| Alexa Fluor 750 | 749 | 775 |
| Alexa Fluor 790 | 782 | 805 |
| IRDye 650 | 651 | 668 |
| IRDye 680RD | 680 | 694 |
| IRDye 680LT | 680 | 694 |
| IRDye 700 phosphoramidite | 680 | 697 |
| IRDye 700DX | 680 | 687 |
| IRDye 750 | 766 | 776 |
| IRDye 800 phosphoramidite | 787 | 812 |
| IRDye 800RS | 770 | 786 |
| IRDye 800CW | 778 | 794 |
| CF ™ 680 | 681 | 698 |
| CF ™ 680R | 680 | 701 |
| CF ™ 750 | 755 | 777 |
| CF ™ 770 | 770 | 797 |
| CF ™ 790 | 784 | 806 |
| Cy7 | 750 | 773 |
| Cy7.5 | 788 | 808 |
| DyLight 775-B2 | 772 | 787 |
| DyLight 775-B3 | 770 | 788 |
| DyLight 775-B4 | 767 | 787 |
| DyLight 780-B1 | 783 | 799 |
| DyLight 780-B2 | 784 | 796 |
| DyLight 780-B3 | 785 | 794 |
| DyLight 830-B2 | 844 | 875 |

A particular embodiment of a NIR fluorescent probe to be used with the nanoparticles of the present invention is indocyanine green (ICG).

ICG is a clinically used dye in NIRF imaging (with an 820 nm emission) and is the only NIRF molecule approved by the US Food and Drug Administration (FDA) and European Medicines Agency (EMA) for human use. ICG is indicated for determining cardiac output, hepatic function and liver blood flow, and for ophthalmic angiography. ICG is used off-label or in research to visualize fluid-filled anatomical structures (for example, blood, cerebrospinal fluid, lymph, or urine) or as a contrast agent for vascular, renal, or excretory pathways (1). In aqueous environments, ICG molecules aggregate and ICG fluorescence readily degrades (reducing the overall fluorescence intensity) (2-5). In blood, ICG binds to plasma proteins, partially and temporary improving its fluorescence intensity, but eventually dissociates and becomes subjected to degradation in aqueous fluid. In vivo ICG fluorescence intensity and duration may vary with fluctuating plasma protein and lipoprotein concentrations and interindividual variation.

The nanoparticles of the present invention may comprise up to about 10% (w/w) of the NIR fluorescent probe, for example up to about 5%, up to about 1%, up to about 0.5%, between about 0.005-5% (w/w) of the NIR fluorescent probe.

C. ICG-LNP

In another aspect, the present invention provides ICG-LNP wherein one or more of the ICG is embedded in the lipid of the nanoparticles.

Liposome-encapsulated ICG (i.e., ICG in the aqueous core of liposomes) (8-12) results in weak interactions between ICG and lipid.

To overcome these limitations, there have been attempts to add ICG to hydrophobic polymers, serum albumin, and liposomes. Not all liposomes and lipid nanoparticles are alike; some may consist of phospholipids with different headgroups and fatty acyl chains, while others may include cholesterol or other additives, all of which can alter a liposome's physiochemical properties (6). The polar headgroup of a lipid affects the particle surface charge and degree of hydration, which impacts the level of in vivo opsonization and complement binding that induces clearance, and the amount of saturation and chain length of the lipid fatty acyl tails affect the lipid phase transition temperature (Tc) by altering the rigidity, thickness, and uniformity of the lipid bilayer (6). Therefore, each variable may impact not only the stability and interactions between ICG and lipid but also the in vivo behavior of the particles.

The present invention provides novel ICG-LNPs with strong (irreversibly bound) ICG-lipid interactions that result from embedding ICG into the lipid particles provided in this invention. Preparation of liposome-encapsulated ICG requires a purification/filtration step to remove free (unencapsulated) ICG, which is unnecessary in this invention due to the substantially to complete 100% embedding efficiency in lipid that is achieved.

One salient feature of the ICG-LNP is that it reduces or even eliminates the deficiencies related to the concentration-dependent self-quenching property of ICG. See FIG. 3. Because of a high degree of overlap between the absorption and emission spectra of ICG, ICG exhibits concentration-dependent fluorescence quenching (self-quenching). It is therefore important to define not only the lipid-ICG interactions but also the optimal density of ICG molecules in lipid that exhibits both maximal fluorescence intensity per ICG molecule and minimal self-quenching. See FIG. 3. Contrary to common fluorescence properties of most infrared dyes, ICG is self-quenched at concentrations as low as a few micromolar ($\mu$M) ICG. While many studies are done with liposomal and lipid-ICG mixtures, none have integrated the self-quenching property, which leads to variable florescence stability, robustness, and more importantly the enhancement achieved here (by minimizing self-quenching). The present invention provides a simple 3-step procedure to generate a stable ICG lipid nanoparticle product for high-resolution NIRF imaging. Kraft J C, Ho R J (2014) Interactions of indocyanine green and lipid in enhancing near-infrared fluorescence properties: the basis for near-infrared imaging in vivo. Biochemistry; March 4; 53(8): 1275-83, the disclosure of which is incorporated by reference in its entirety.

In some embodiments, at least about 90%, 91%, 92%, 93%, 94%, 95%, 96%, 97%, 97.5%, 98%, 98.5%, 99%, 99.5% or 99.9% of ICG is embedded into the lipid membrane. In some embodiments, there is a +/−0.1%, +/−0.2%, +/−0.3%, +/−0.4%, +/−0.5%, +/−0.6%, +/−0.7%, +/−0.8%, +/−0.9%, +/−10.0% deviation. In some embodiments, at least 97.8+/−0.6% is embedded in the lipid membrane.

In some embodiments, substantially or completely 100% of ICG is embedded in the lipid membrane.

In some embodiments, there is less than 5%, 4%, 3%, 2%, 1%, 0.9%, 0.8%, 0.6%, 0.5%, 0.4%, 0.3%, 0.2%, 0.1%, 0.01%, or 0.001% of ICG that is encapsulated in the aqueous core of the lipid nanoparticle.

In some embodiments, no detectable amount of said ICG is encapsulated in the aqueous core of the lipid nanoparticle.

The amount or percentage of the ICG embedded in the lipid membrane or encapsulated in the aqueous core of the lipid nanoparticle is measured using methods known in the art, such as Bilayer/water partitioning studies by equilibrium dialysis, Joguparthi V, Feng S, Anderson B D. Determination of intraliposomal pH and its effect on membrane partitioning and passive loading of a hydrophobic camptothecin, DB-67. Int J Pharm. 2008 Mar. 20; 352(1-2):17-28. Epub 2007 Oct.

12. PubMed PMID: 18065174; PubMed Central PMCID: PMC2277365, the disclosure of which is incorporated by reference in its entirety.

In some embodiments, the ratio of ICG vs. the lipid is from about 0.3 to about 0.2, 0.1, 0.09, 0.08, 0.07, 0.06, 0.05, 0.04, 0.03, 0.02, or 0.001 mol/mol.

In some embodiments, there is ~10-fold lower ICG dose used in the lipid-embedded composition compared to aqueous ICG (used clinically), as being reflected in the amount of ICG-LNPs used per patient/procedure.

In some embodiments, The nanoparticles of the present invention may comprise at least one magnetic probe detectable by magnetic resonance imaging (MRI), in addition to the NIR fluorescent probe.

In some embodiments, the magnetic probe is bound to the outer surface of the nanoparticles, either covalently or non-covalently. In other embodiments, the magnetic probe is contained embedded within the inner core of, or coated by, the nanoparticles.

Magnetic nanoparticles include particles that are permanently magnetic and those that are magnetizable upon exposure to an external magnetic field, but lose their magnetization when the field is removed. Materials that are magnetic or magnetizable upon exposure to a magnetic field that lose their magnetic properties when the field is removed are referred to as superparamagnetic material. Examples of suitable superparamagnetic materials include, but are not limited to, iron, mixed iron oxide (magnetite), or gamma ferric oxide (maghemite) as well as substituted magnetites that include additional elements such as zinc. Superparamagnetic particles may range in size from about 1 nm to about 20 nm, for example between about 1-10 nm, between about 5-20 nm.

Preparation of superparamagnetic particles, and also nanoparticles comprising such superparamagnetic particles can be performed by methods known in the art, for example, as described in De Cuyper et al., 1988, Eur Biophys J, 15:311-319. Additional methods are described, for example, in U.S. Pat. Nos. 7,175,912, 7,175,909 and US 20050271745, as well as WO2014002100 A1, all incorporated by reference in their entities.

D. Properties of ICG-LNP

In general, the present invention provides lipid-associated particles, such as indocyanine green particles, with increased stability and in vivo capabilities (see e.g., FIGS. 12 and 13), for enhanced functional high-resolution near-infrared fluorescence medical imaging of lymphatic vessels, lymph nodes, lymphatic abnormalities, tumors, and inflammation (see e.g., FIGS. 4-11 and 16-20).

The fluorescence intensity achieved with the particles provided in the present invention is above and beyond that previously achieved with liposome or other polymeric carriers containing indocyanine green (ICG).

The present invention provides a unique, simple, and scalable, composition and preparation method that is developed for bio-compatible indocyanine green (ICG) nanoparticles that enhance ICG intensity by 4.5-fold or more, thus improving image resolution and sensitivity to detect occult tissues and cells with near-infrared fluorescence (NIRF) bioimaging. This 4.5-fold or more ICG fluorescence intensity amplification is unprecedented and novel. Unlike previously described liposome-encapsulated ICG compositions, and limited lipid-ICG accidental associations, which involve cumbersome and resource-intensive preparation procedures, the composition and method described herein provide a simple and yet effective 3-step preparation procedure (See e.g., FIG. 1) that exclusively stably embeds 100% of ICG in lipid and brings foreword the highest intensity potential in biologic fluid and solutions. This combination of ICG fluorescence intensity and stability enhancement (see e.g., FIGS. 3, 12, and 13) resulting from a simple and efficient preparation procedure has not been previously achieved.

In some embodiments, the particles provided herein have at least, 2, 3, 4, 4.5, 5, 6 fold, or even higher fold enhancement of ICG fluorescence intensity versus that of aqueous ICG (13), which has not been achieved with any reported carriers including liposomes.

Figure 11:
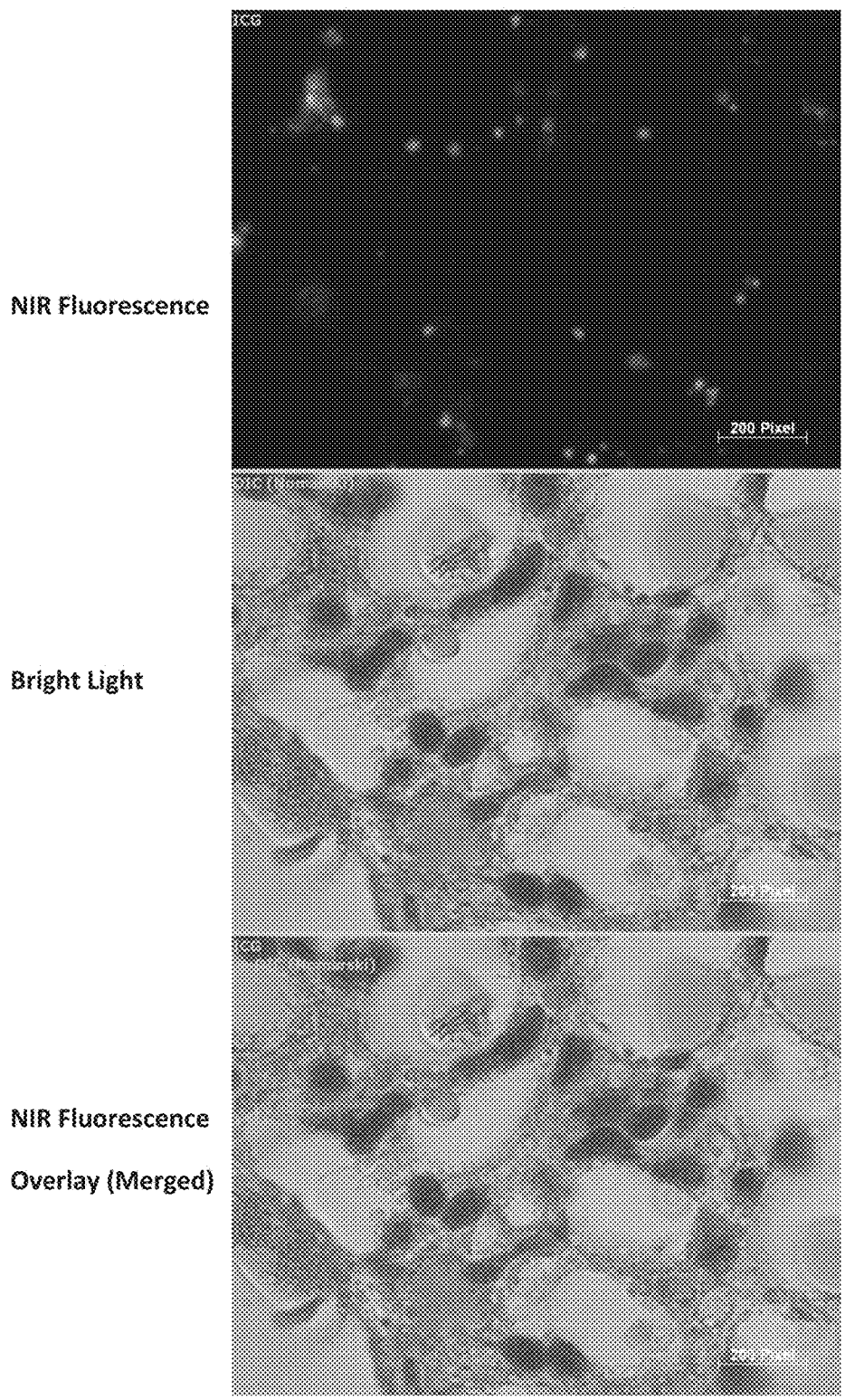
FIG. 11 depicts NIR fluorescence microscopy of a tissue slice from a mouse's axillary lymph node that was dosed with ICG-LNP subcutaneously in the foot. Punctuated fluorescence indicates the stability of ICG-LNP particles in vivo and access to the interior of lymph node and lymphoid tissue following extensive travel through the lymphatic system from the injection site. Some ICG-LNPs are intracellular and associated with macrophages and dendritic cells.
Figure 12:
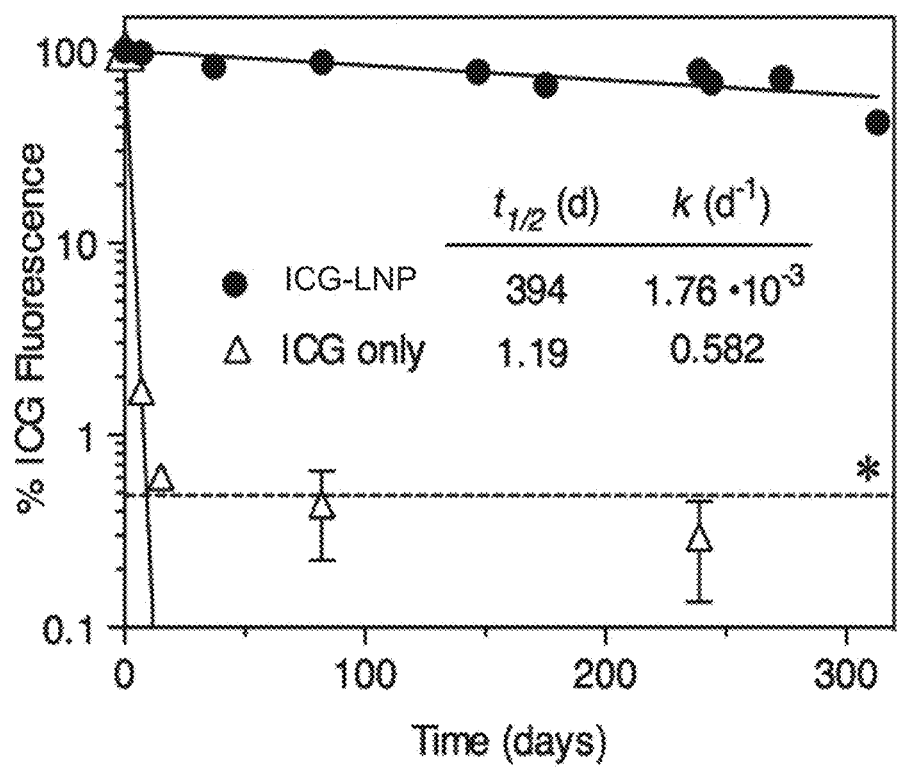
FIG. 12 depicts stability of ICG-LNPs in storage. ICG-LNPs and free ICG were stored in the dark at 4° C. for up to 313 days, and ICG fluorescence was analyzed at indicated time points: (Δ) free ICG and (●) ICG-lipid nanoparticles (ICG-LNPs). The time course data were analyzed on the basis of an exponential decay model, and the half-life, $t_{1/2}$ (days), and rate constant, k (inverse days), values are listed. The dashed line indicates the limit of detection. Each data point is the mean±SD of three to eight replicates.
Figure 13:
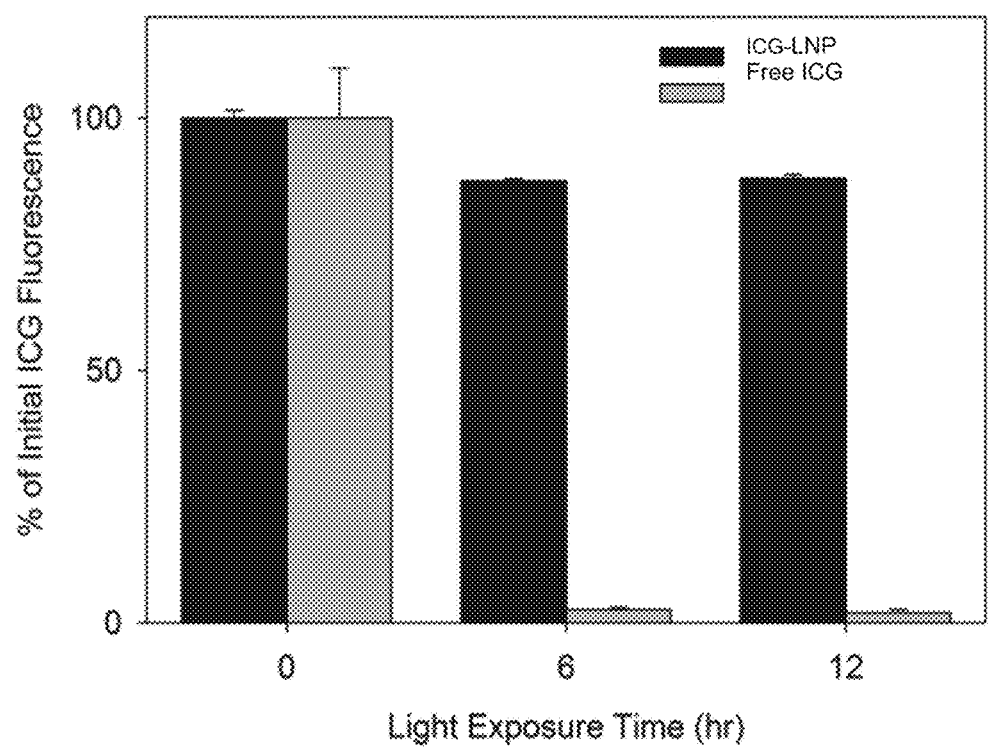
FIG. 13 shows ICG-LNP reduces ICG fluorescence quenching due to light exposure. ICG-LNP and free ICG were exposed to overhead fluorescent light for 12 h. ICG fluorescence was recorded at 6 and 12 h. Black bars represent data for ICG-LNPs and gray bars data for ICG only. Each data point is the mean±SD of eight replicates.

Attempts have been made to encapsulate ICG or bind it to proteins and have not achieved this fluorescence intensity enhancement and the accompanying stability of this invention (see e.g., FIGS. 11-13). Many scientists have encapsulated too high of concentrations of ICG (10-12, 14), which actually detracts from the fluorescence intensity of ICG due to concentration-dependent self-quenching of the fluorescence signal.

Figure 2:
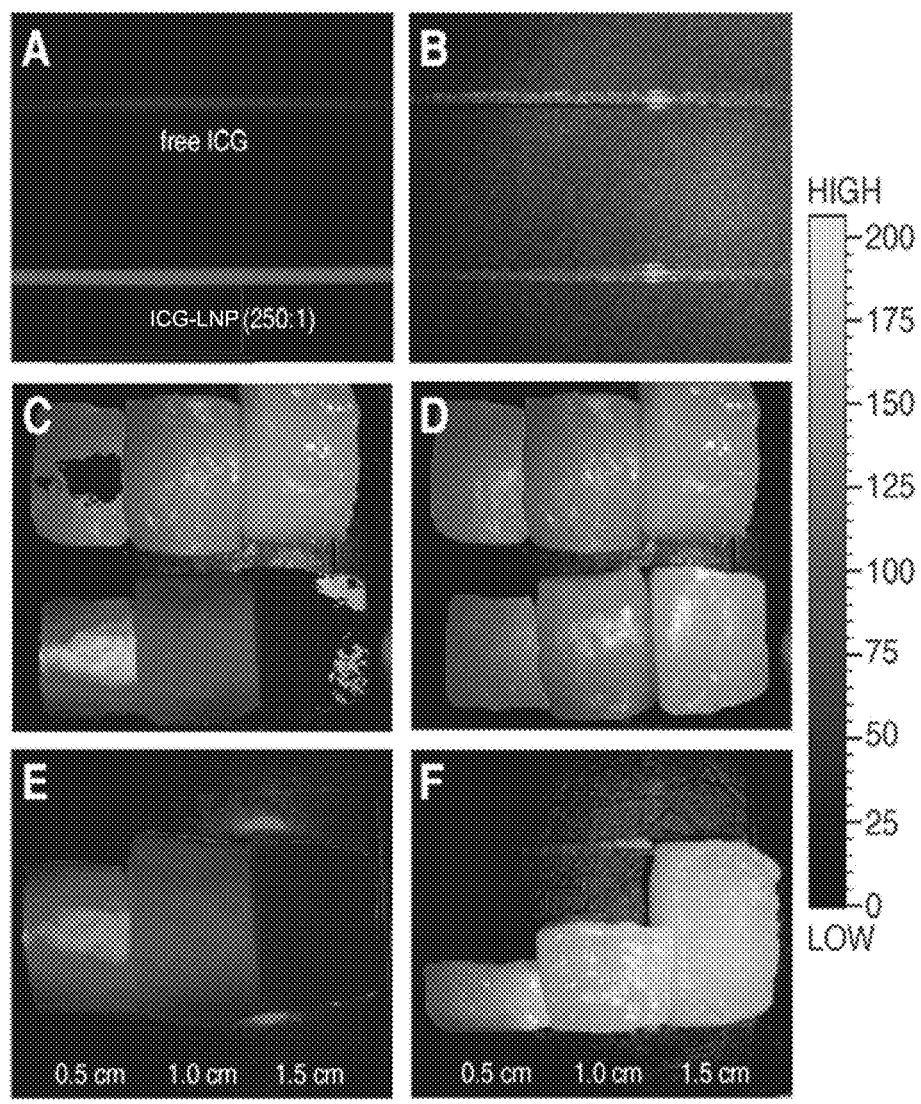
FIG. 2 depicts fluorescence intensity of ICG-LNPs vs. free ICG detected through muscle tissue. (A) NIR fluorescence image intensity of capillary tubes filled with 30 µM free ICG (top) and ICG-LNPs (bottom). (B) White light image of the two identical capillary tubes filled with different formulations of ICG in panel A. (C) NIR fluorescence image overlaid on a visual light photograph of capillaries filled with free ICG (top) or ICG-LNPs (bottom) and placed underneath 0.5, 1.0, and 1.5 cm (from left to right, respectively) chicken breast tissue cuboids. (D) Visible light image of chicken breast tissue cuboids in panel C. (E) NIR fluorescence image overlaid on a visual light background of an ICG-LNP capillary placed underneath 0.5, 1.0, and 1.5 cm chicken breast tissue cuboids. (F) Side view of tissue cuboid thickness.

The high amplification of ICG fluorescence intensity provided by the nanoparticles provided herein allows light transmittance through tissue thicknesses of 1 cm or more (see e.g., FIG. 2). This is a significant improvement over that achieved by free ICG (13), which only penetrates tissue approximately 0.5 cm (see e.g., FIG. 2). This enhanced tissue penetration depth as a result of the amplified fluorescence intensity is another non-obvious and novel component of this invention.

Specifically, in US Pat. Pub. No US2014/0341813A1, a pH-gradient method is presented using a chaotropic agent (e.g., urea, guanidine, iodine, or other ions) to prevent J-aggregation of ICG and allow high concentrations of the monomeric form of ICG ($\geq 1$ mM ICG) to be encapsulated in the aqueous core of liposomes. However, it is known that in water ICG begins to form aggregates at concentrations of ~5 µM ICG (2, 15-17). Although a chaotropic agent is used to reduce the interaction between water molecules and ICG that leads to destabilization and aggregation, the concentrations described in this patent application (at least 200-fold higher than those that cause ICG aggregation) may be susceptible to concentration-dependent quenching and loss of fluorescence intensity. In fact, although NIRF imaging is a suggested application/field, the inventors note in item [0135], "In the present invention, quenching due to the accumulation of the dye is caused by suppressing leakage of the dye . . . " Thus, fluorescence intensity emission from such particles would be very limited.

In some embodiments, the nanoparticle has a fluorescence intensity between 2- and 10-fold higher than that of aqueous ICG.

In some embodiments, the nanoparticle has a fluorescence intensity between 4- and 5-fold higher than that of free ICG in aqueous solution.

The nanoparticle provided herein has superior stability in comparison to the particles known in the art (see e.g., FIGS. 11-13).

In addition to optimizing the ICG-LNP formulation to achieve maximal fluorescence yield, stability against environmental effects is also necessary. Light causes ICG to produce singlet oxygen that chemically decomposes ICG through a dioxetane reaction (the polymethine chain of ICG cleaves into two carbonyl products, which may be cytotoxic) (18, 19). With clinical settings and surgical fields normally well lit, such light decomposition is challenging to avoid.

In its currently supplied form, free ICG in aqueous solution decomposes from light in a matter of seconds. The present invention discloses that embedding ICG into lipids shields against light degradation (see e.g., FIG. 13). ICG-LNPs can be exposed to light for several hours at room temperature and retain nearly all of their original fluorescence intensity (see e.g., FIG. 13).

The nanoparticles provided retain fluorescence integrity exceeds those from other reports such as 42 days at room temperature (9) and 70 days at 4° C. (20) (see e.g., FIG. 12).

In some embodiments, when stored in the dark at 4° C. in an aqueous suspension, the ICG particle product provided herein retains its fluorescence integrity for at least about 2, 3, 4, 5, 6, 7, 8, 9, 10, 11, or 12 months, or longer (see e.g., FIG. 12), when stored in the dark, at 4° C. in aqueous suspension. In general, there is at least at least between about 50% to about 60%, 65%, 70%, 75%, 80%, 85%, 90%, 95%, or 100% of fluorescence retained.

In some embodiments, the ICG-LNPs provided are stable in serum with between about 50% to about 60%, 65%, 70%, 75%, 80%, 85%, 90%, 95%, or 100% of its initial fluorescence retained in heat-inactivated rat serum after 6 h, at 25° C. In some embodiments, the ICG-LNPs provided are stable in serum with 94±0.6% of its initial fluorescence retained in heat-inactivated rat serum after 6 h, at 25° C.

In some embodiments, the ICG-LNPs provided are stable in serum with at least about 90%, 91%, 92%, 93%, 94%, 95%, 96%, 97%, 98%, 99%, or 100% of its initial fluorescence retained in heat-inactivated rat serum for a period of time, such as about 1 h, 2 h, 3 h, 4 h, 4 h, 5 h, 6 h, 8 hr, 10 hr, 12 hr, 14 h, 16 h, 18 h, 20 h, 24 h, or longer.

In some embodiments, the nanoparticle has a fluorescence intensity between 50% and 100% of its original fluorescence intensity after being stored at 4° C. in the dark for over 300 days.

In some embodiments, the nanoparticle has an average half life of between 0.5 to 1, 2, 3, 4, 5, 6, 7, 8, 9, or 10 hr, or longer.

Further stabilization of ICG particle products provided is achieved by lyophilization with a cryoprotectant such as trehalose or sucrose that retains the particle characteristics upon hydration with water.

Taken together, the observed light, storage, and serum stability indicate ICG-LNPs have robust stability for clinical use, especially for imaging the lymphatic system where lymph contains approximately a 2-fold lower serum protein concentration than blood.

The LNPs provided is more potent than other ICG agents known in the art due to its high fluorescence intensity. By "potent" herein is meant being able to emit higher fluorescence with the same or less ICG molecules after administered to a tissue or organ to generate an image for intended purpose.

In some embodiments, the composition is potent at less than about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, 0.02 mg/kg, or 0.01 mg/kg ICG dose.

In some embodiments, the composition is potent between about 0.01 mg/kg to about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, or 0.02 mg/kg, inclusive, ICG dose.

In some embodiments, the composition is potent at about 0.05 mg/kg to 0.5 mg/kg ICG dose, inclusive.

Potency of the compositions or ICG-LNP provided herein is measured using methods known in the art. For example, fluorescence fold-enhancement of nanoparticles vs. aqueous ICG is compared among published literature values.

One well known trait of liposomes is that they accumulate in liver tissue (7). However, the ICG-LNPs of this invention do not accumulate in the liver, but are almost completely eliminated through the hepato-biliary tract into the intestine, a distinguishing and novel attribute of these ICG particles (see e.g., FIG. 19).

The ICG particles provided herein are more stable than any reported composition and method. Moreover, these particles can be used to identify tumors (see e.g., FIG. 4) and sites of inflammation with lymphatic vascularization (see e.g., FIGS. 5-8 and 20). The particles developed in this invention stably and specifically transport a NIRF molecule to the lymphatic system to allow for NIRF imaging.

II. Methods of Making ICG-LNPs

In another aspect, the present invention provides a simple solution to address the limitation of ICG aqueous instability, aggregation, and degradation, and allows for better resolution imaging of deeper tissue levels than ICG alone. In the methods provided in this invention, no separation procedures are necessary due to 100% (or proximately 100%) embedding of ICG into lipid, strong ICG-lipid binding interactions are produced by a simple 3-step preparation procedure (see e.g., FIG. 1), and ICG self-quenching is reduced to maximally amplify ICG fluorescence intensity yield (see e.g., FIG. 3).

The present invention provides a simple/streamlined preparation procedure that involves only 3 steps: (1) mixing of indocyanine green (ICG) and lipid molecules together in an organic solvent, (2) evaporating organic solvent containing well-mixed lipid and ICG, and (3) particle size reduction of hydrated ICG-lipid mixture, and does not require filtration/purification/separation steps to remove free unincorporated ICG due to complete ICG embedding in ICG-lipid nanoparticles (see e.g. FIG. 1).

In some embodiments, the method for preparation of nanoparticles, comprises: (a) mixing an indocyanine green (ICG) and lipid molecules together in an organic solvent; (b) evaporating the organic solvent to create a thin film comprising said lipid molecules and said ICG; and (c) hydrating said thin film with a buffered salt; and (d) reducing particle size using ultrasound energy or homogenization procedures to reduce particle size of said thin film hydrated with said buffered salt.

The methods provided herein differ from methods known in the art that have neglected to mix together ICG and lipids in organic solvent as the initial preparation step prior to forming a lipid thin film, which is essential to stably embed ICG into lipid. Instead, methods known in the art add an aqueous solution of ICG to an already formed lipid thin film that results in inefficient encapsulation of ICG in the aqueous core of liposomes.

In some embodiments, the lipid molecules comprise 1,2-Distearoyl-sn-glycero-3-phosphocholine (DSPC), and 1,2-distearoyl-sn-glycero-3-phosphoethanolamine-N-methoxy-polyethylene glycol-2000 (DSPEmPEG2000).

In some embodiments, the organic solvent comprises ethanol, methanol, chloroform, ethyl acetate, or DMSO.

In some embodiments, the lipid nanoparticle is suspended in a salt composition comprising a biocompatible buffer, such as one has a pH 5-8 and Osm ~303 mOSM. Examples of such buffer include normal saline, Ringer's, dextrose 5% in water, or a buffer of 0.9% NaCl and about 20 mM NaHCO$_3$.

In some embodiments, the buffered salt comprises about 0.9% NaCl and about 20 mM NaHCO$_3$.

In some embodiments, the method does not comprise a filtration step, a purification step, or a separation step, or a combination thereof.

In some embodiments, the method does not include any filtration step, purification step, or separation step.

US Pat. Pub. No US2014/0341813A1 discloses a pH-gradient method using a chaotropic agent (e.g., urea, guanidine, iodine, or other ions) to prevent J-aggregation of ICG and allow high concentrations of the monomeric form of ICG ($\geq$1 mM ICG) to be encapsulated in the aqueous core of liposomes. However, the preparation procedure described in the referenced patent application is cumbersome ($\geq$5 steps) for a number of other reasons, including the need to use a pH-gradient, the instability of ICG in aqueous solution (despite the presence of a chaotropic agent), and the required step of filtration and purification due to incomplete encapsulation of all free ICG (only a 27.4% encapsulation ratio is reported).

The preparation procedure disclosed herein is much more simplified, as it involves no pH-gradient or purification step but only three simple steps: mixing, drying, and hydration/size reduction.

In some embodiments, the lipid nanoparticle is suspended in a salt composition comprising about 0.9% NaCl and about 5-50 mM (such as 5, 10, 15, 20, 25, 30, 35, 40, 45, or 50 mM) $NaHCO_3$.

The methods and compositions provided herein is based on the unexpected discovery of the simple and scalable 3-step preparation method and composition that enables nearly 100% embedding of indocyanine green (ICG) into lipid to form stabilized lipid nanoparticles (LNPs).

This unique method of ICG binding to lipid greatly enhances the stability and near-infrared fluorescence (NIRF) intensity of ICG, beyond what could be achieved with free ICG, allowing deeper tissue imaging. While the formulation of the LNPs of this invention is similar to that of liposomes, the present invention discloses novel attributes that were not obvious in early physiochemical and in vivo studies of liposomes, and these ICG-LNPs exhibit superior attributes to other reported ICG liposomes, namely (1) the 100% embedding efficiency that precludes any purification steps, (2) a simple 3-step preparation procedure that produces highly stable particles, and (3) optimization of ICG spectroscopic properties to prevent self-quenching of ICG fluorescence emission and greatly enhance ICG's fluorescence intensity yield. Integrating these components into a single system with a highly specialized composition is non-obvious and provides an unprecedented synergy that increases the in vivo NIR imaging time and resolution behavior. Specifically, the composition matter in this invention is uniquely suited for uptake, retention, and widespread distribution in lymphatic vessels and lymph nodes for mapping the lymphatic architecture and network, identifying lymphatic pathologies and abnormalities, identifying tumors with lymphatic vascularization, identifying sites of inflammation with tertiary lymphoid organs, and drug delivery to the lymphatic system and lymphatic-associated pathologies.

The methods for preparation of nanoparticles provided by the present invention provided various novel aspects and advantages over methods known in the art, such as: (1) the integration of composition and three preparation steps to produce a physically stable product with unique properties (stable and high ICG fluorescence yield); (2) the integration of ICG spectroscopic properties to enhance potency; (3) the simple 3-step procedure that avoids free ICG removal, allowing to lower the overall cost and control potential contaminations due to complex multiple-step procedures; (4) the embedding of the fluorescent molecule (indocyanine green (ICG)) into ICG-lipid nanoparticles (ICG-LNPs) that enhances the fluorescence intensity well above that achievable with aqueous ICG encapsulated in liposomes or lipid vesicles; (5) the ~10-fold lower ICG dose used in the lipid-embedded composition compared to aqueous ICG (used clinically) for in vivo near-infrared (NIR) imaging results in both higher resolution and fluorescence intensity; and (6) the unique composition, size, and surface properties that allows for nearly 100% embedding of ICG into the lipid membrane, enhanced stability (both in storage and in vivo), and capabilities important to in vivo functional medical imaging of the lymphatic system.

III. Pharmaceutical Formulations and Administration

The present invention further relates to a pharmaceutical formulation comprising a compound of the invention or a pharmaceutically acceptable salt thereof, and one or more pharmaceutically acceptable carriers.

A. Contrast Agent

The nanoparticles provided herein can be used as a contrast agent for fluorescence imaging or for photoacoustic imaging because the particle contains ICG and can absorb near infrared light to emit fluorescence or an acoustic wave. In addition, the particle can be used as a contrast agent for visual detection because ICG has a green color.

By "contrast agent" herein is meant a substance capable of causing a difference in contrast between a tissue or molecule which one wishes to observe, the tissue or molecule being present in a specimen, and a tissue or molecule around the tissue or molecule to improve the sensitivity of the detection of morphological information or positional information about the tissue or molecule which one wishes to observe.

By "fluorescence imaging" or "photoacoustic imaging" herein is meant that the tissue or molecule is imaged with, for example, a fluorescence-detecting apparatus or a photoacoustic signal-detecting apparatus.

A contrast agent according to this embodiment includes the particle according provided herein and a dispersion medium in which the particle is dispersed. The dispersion medium is a liquid substance for dispersing the particles, and examples thereof include physiological saline and distilled water for injection. In addition, the contrast agent may have a pharmacologically acceptable additive such as table salt or glucose. The contrast agent may be such that the particle according to this embodiment is dispersed in the dispersion medium in advance, or may be used as described below. The particle according and the dispersion medium are packages into a kit, and the particle is dispersed in the dispersion medium before administration into a living organism, such as a human being.

IV. Kits of the Invention

The instructions relating to the use of composition generally include information as to dosage, dosing schedule, and route of administration for the intended treatment. The containers of composition may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

V. Medical Use

Most fluorescence medical imaging (less than 600-700 nm) is limited by light absorption and scattering by blood, tissue, and fat in the body. Because indocyanine green (ICG) emits fluorescence at 820 nm, which is in the middle of the 700-900 nm range where the light absorption coefficients for blood, water, tissue, and lipids are at their lowest, this near-infrared (NIR) compound overcomes biological tissue interference.

Figure 8:
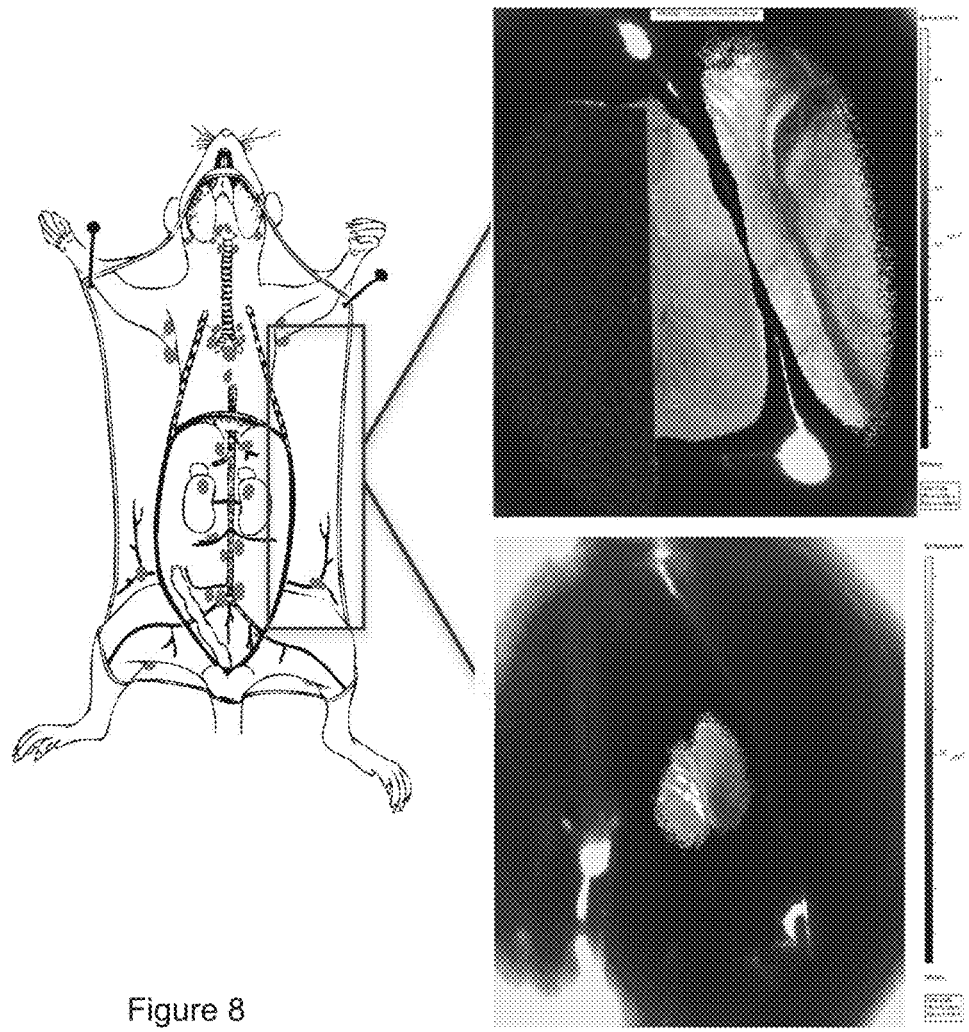
FIG. 8 depicts lymph vessel tracking and vessel dilation detected with ICG-LNP in the lymphatic vessel that connects the left subiliac (inguinal) lymph node to the left axillary lymph nodes in two separate mice.
Figure 9:
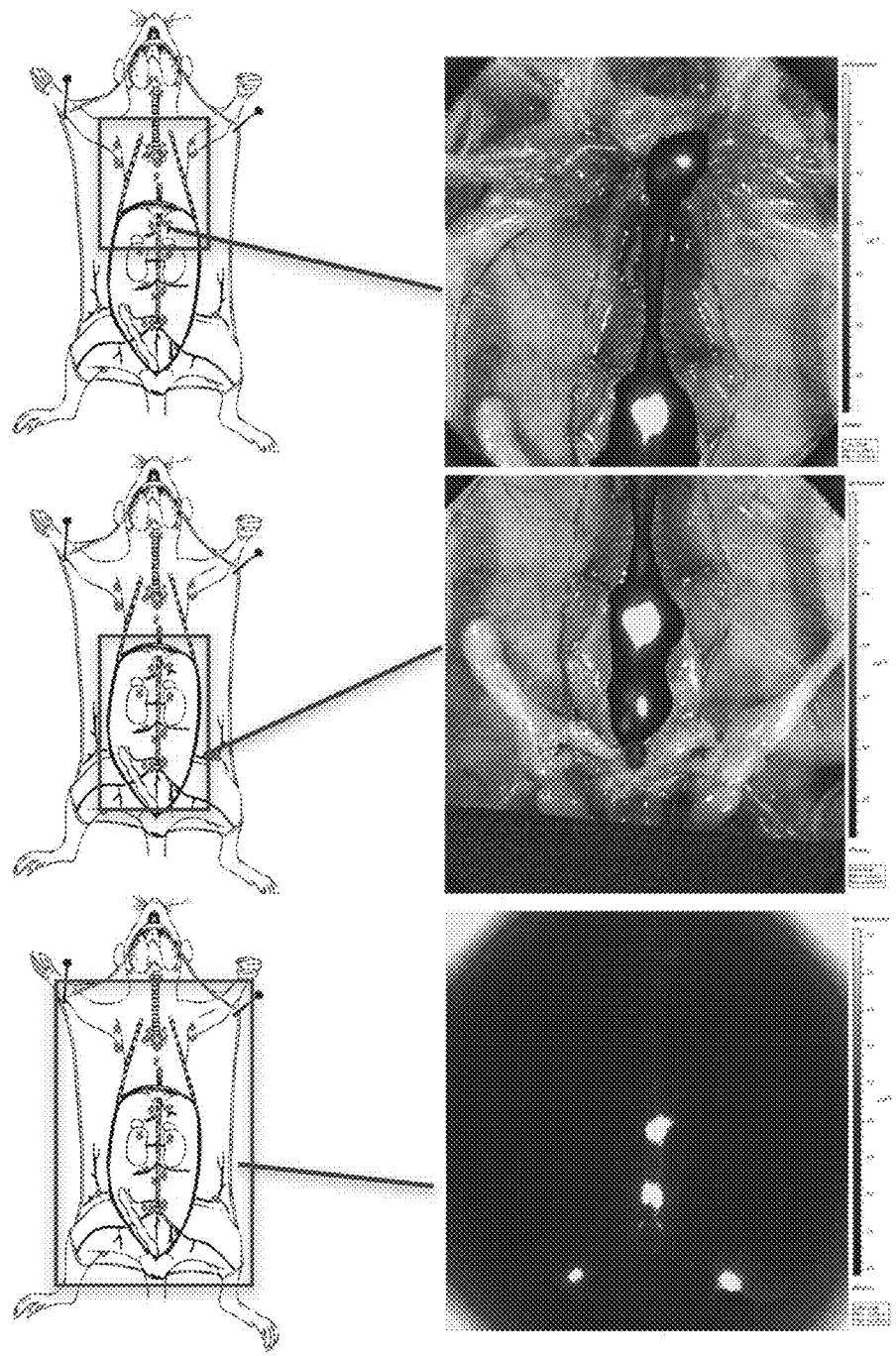
FIG. 9 depicts high-resolution images of medial iliac lymph nodes, cisterna chyli, and thoracic lymphatic duct in mice detected with ICG-LNPs.
Figure 10:
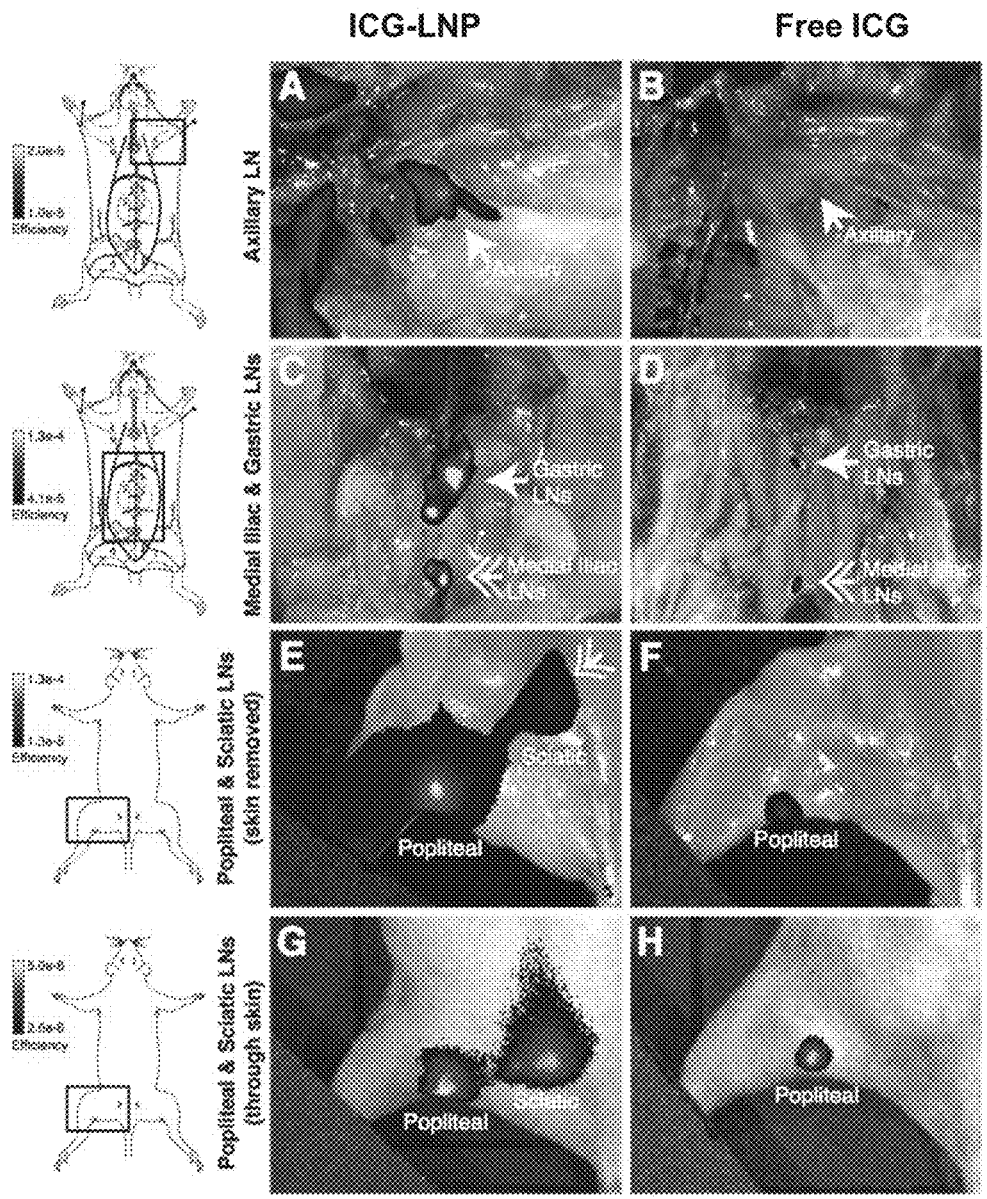
FIG. 10 depicts NIR fluorescence of ICG-LNP vs. free ICG from lymph nodes following subcutaneous foot injection. (A, B) Axillary, (C, D) medial iliac & gastric, (E, F, G, H) popliteal & sciatic LNs.

Following subcutaneous injection, ICG stably embedded into ICG-LNPs is optimized to remain in the lymphatic system without leaching out of the lymph vessels into surrounding tissues as free ICG would (see e.g., FIGS. 8 and 9).

ICG-LNPs may be used by physicians for an array of clinical applications ranging from surgery to diagnosis and drug delivery. Specifically, it could be used to identify lymphatic vessels and lymph nodes (LNs) in surgery (see e.g., FIGS. 9 and 10), to identify lymphatic abnormalities (see e.g., FIGS. 5-8), visualize sentinel LNs of solid tumors, visualize tumors with lymphatic vascularization (see e.g., FIG. 4), visualize sites of inflammation with tertiary lymphoid organs (see e.g., FIGS. 5-8), and delivery of drug to lymphatic vessels, nodes, and pathologies.

More specifically, ICG is the only NIR fluorophore approved by the US Food and Drug Administration (FDA) and European Medicines Agency (EMA) for human use. To image lymphatic vasculature, ICG is currently used clinically by dissolving pure ICG solute in aqueous solution and injecting subcutaneously. Its high binding affinity to albumin enables it to be taken up into the lymphatic vessels, however, this albumin binding is not stable and is reversible, and ICG disassociates from albumin and leaks out of lymphatic capillaries due to concentration gradient forces, and is exposed to aqueous environments in which ICG degrades. By stably embedding ICG into lipid of LNPs, this (1) stabilizes ICG through irreversible lipid binding, (2) enhances its fluorescence yield and duration of high fluorescence intensity, and (3) prevents it from dissociating from the particle and leaking out of the lymphatic vasculature due to the lipid nanoparticle size.

ICG-LNPs remain in the lymphatic vasculature far downstream of the injection site and accumulates in lymph nodes (LNs), allowing for widespread high-resolution NIR fluorescence imaging that is specific to the lymphatic system and significantly more intense and stable than the free ICG composition used clinically as well as other nanoparticle preparations of ICG such as ICG encapsulated in the aqueous core of liposomes (8-12, 21) (US Pat. Pub. No US2014/0341813A1).

Furthermore, the simple and efficient preparation procedure disclosed in this invention, which does not involve any costly and time-consuming separation or purification steps and allows for nearly 100% of ICG to become embedded into lipid, will be useful for large-volume manufacturing scale-up and production.

Due to the particle stability that results from this unique and simple 3-step preparation method and composition, consistent and widespread high-resolution images of the lymphatic as well as blood vessel architecture are created (see e.g., FIGS. 5-10, 16, 19, and 20) that can be used to diagnose, assess, and monitor diseases of the lymphatic system as well as distinguish between normal and aberrant lymphatic structure and function. Systemic blood distribution can be maintained with these particles to detect tissue abnormalities in highly perfused tissues and organs, such as the liver (see e.g., FIG. 18).

In one aspect, the present invention provides nanoparticles with an enhancer/stabilizer of a product (ICG) clinically used for NIRF imaging in humans; as such this technology could be used to enhance ICG stability and fluorescence intensity to improve NIRF imaging with existing NIR imaging instruments.

ICG-LNP is used as a novel diagnostic imaging tool that improves NIRF imaging capabilities to identify/visualize in a subject, (such as a human being), (1) lymphatic and blood vessels and nodes during surgery, (2) lymphatic and vascular abnormalities, (3) sentinel lymph nodes of solid tumors, (4) tumors with lymphatic or general vascularization, and (5) sites of inflammation with tertiary lymphoid organs or in tissues.

By "subject" herein is meant a human or non-human animal, including but not limited to mammals such as a dog, cat, horse, cow, pig, rabbit, guinea pig, sheep, goat, primate, rat, and mouse.

Additionally, conjugation of ICG-LNPs to other hydrophobic molecules, such as the molecules listed in Table 6, could be used to enhance their stability and for drug delivery to lymphatic vessels, nodes, and pathologies.

In the treatment of lymphatic disease, NIRF imaging is a highly sought after tool to guide diagnosis and treatment. Use of the ICG-LNPs in this disclosure improves the capabilities of NIRF imaging by diversifying and advancing its robustness and utility in clinical settings.

Figure 18:
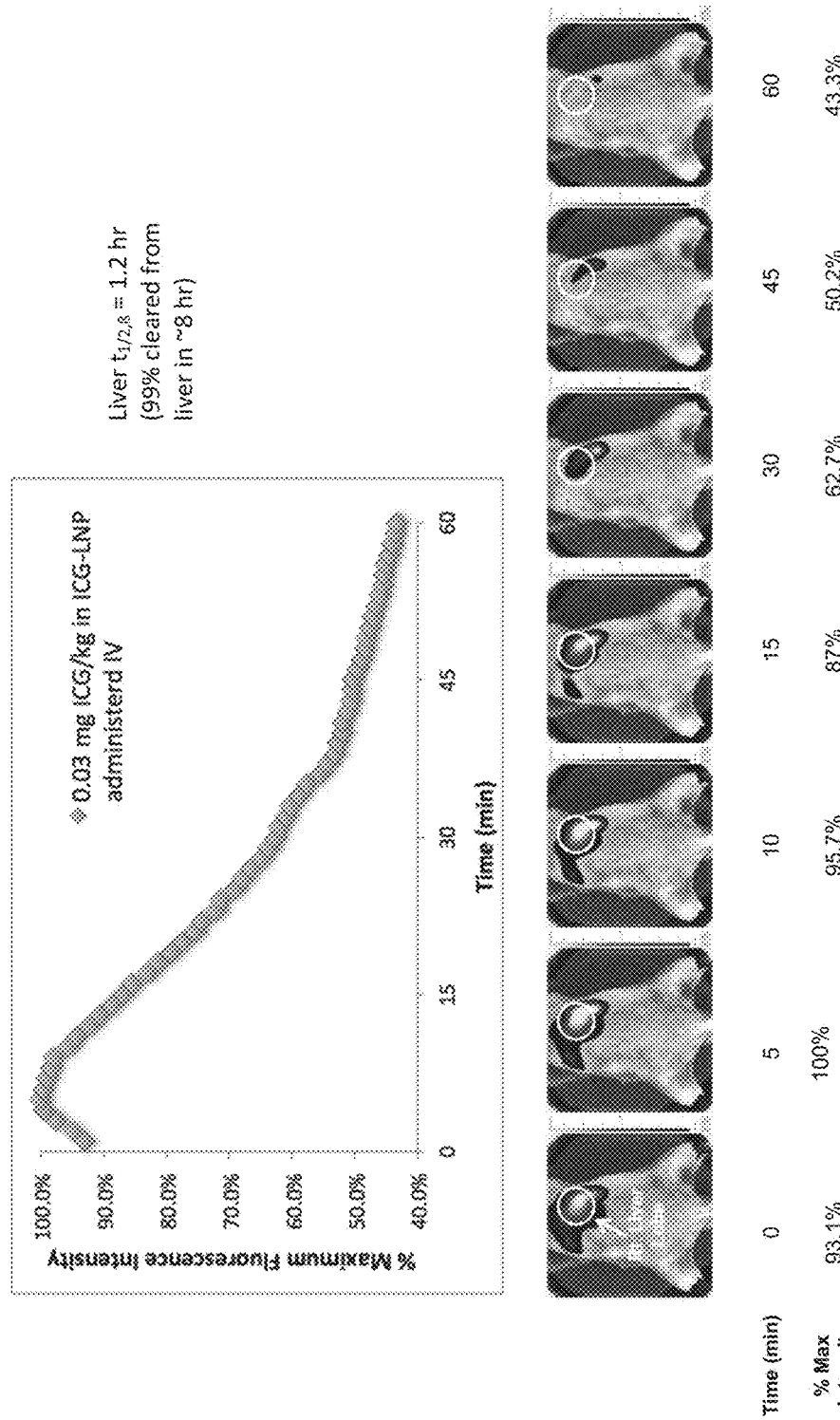
FIG. 18 depicts liver pharmacokinetics detected through skin following intravenous tail vein injection of ICG-LNP. It shows that when ICG-LNP is injected IV in a mouse's tail vein, it is readily eliminated from the liver with a terminal elimination half-life of 1.2 hours. Thus, ICG-LNPs are completely cleared from the liver in approximately 8 hours (~7 half-lives). This is very different behavior from traditional liposomes that linger in the liver due to uptake by Kupffer macrophages (Daemen T 1997 Hepatology 26(2): 416-423). From the liver, ICG-LNP are eliminated through the biliary track into the intestine. Thus, ICG-LNP could be used to assess hepato-biliary function.
Figure 19:
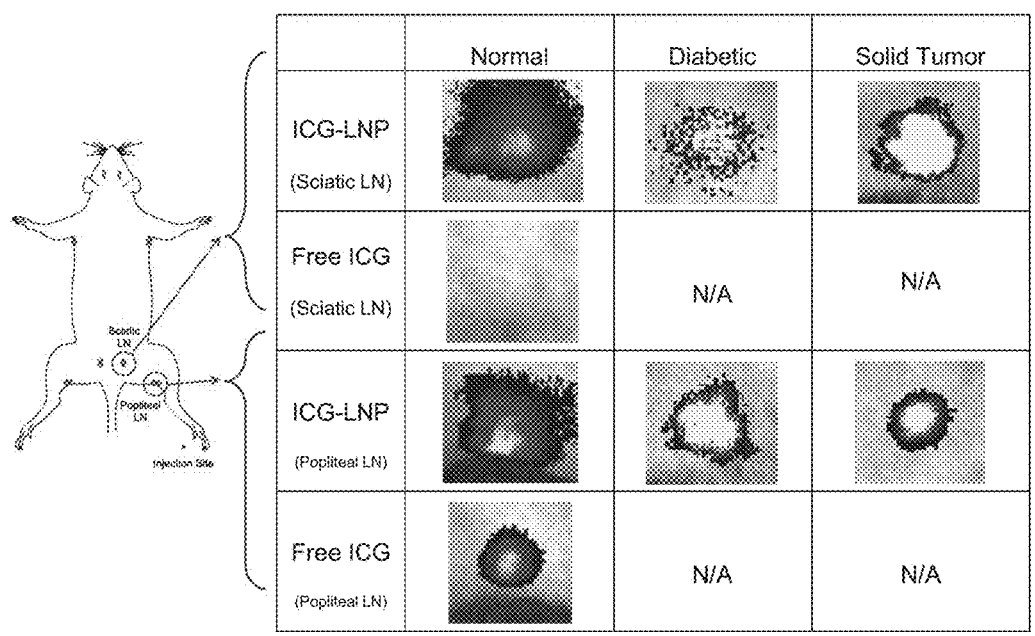
FIG. 19 depicts in vivo fluorescence intensity through skin from lymph nodes (popliteal and sciatic) following subcutaneous injection of free ICG vs. ICG-LNP in mouse foot in normal, diabetic, or solid tumor-bearing mice. It shows the ability of ICG-LNP to detect popliteal and sciatic lymph nodes (1st and 2nd draining lymph nodes, respectively) from the subcutaneous foot injection site in normal and disease (diabetic, tumor-bearing) mice. As indicated above in FIG. 1 and in Tables 2 and 3, ICG-LNP may be used to assess lymphatic function in these disease models. In the normal mouse, the brighter images obtained with ICG-LNP compared to free ICG demonstrates the enhanced fluorescence intensity and higher resolution that is possible.
Figure 20:
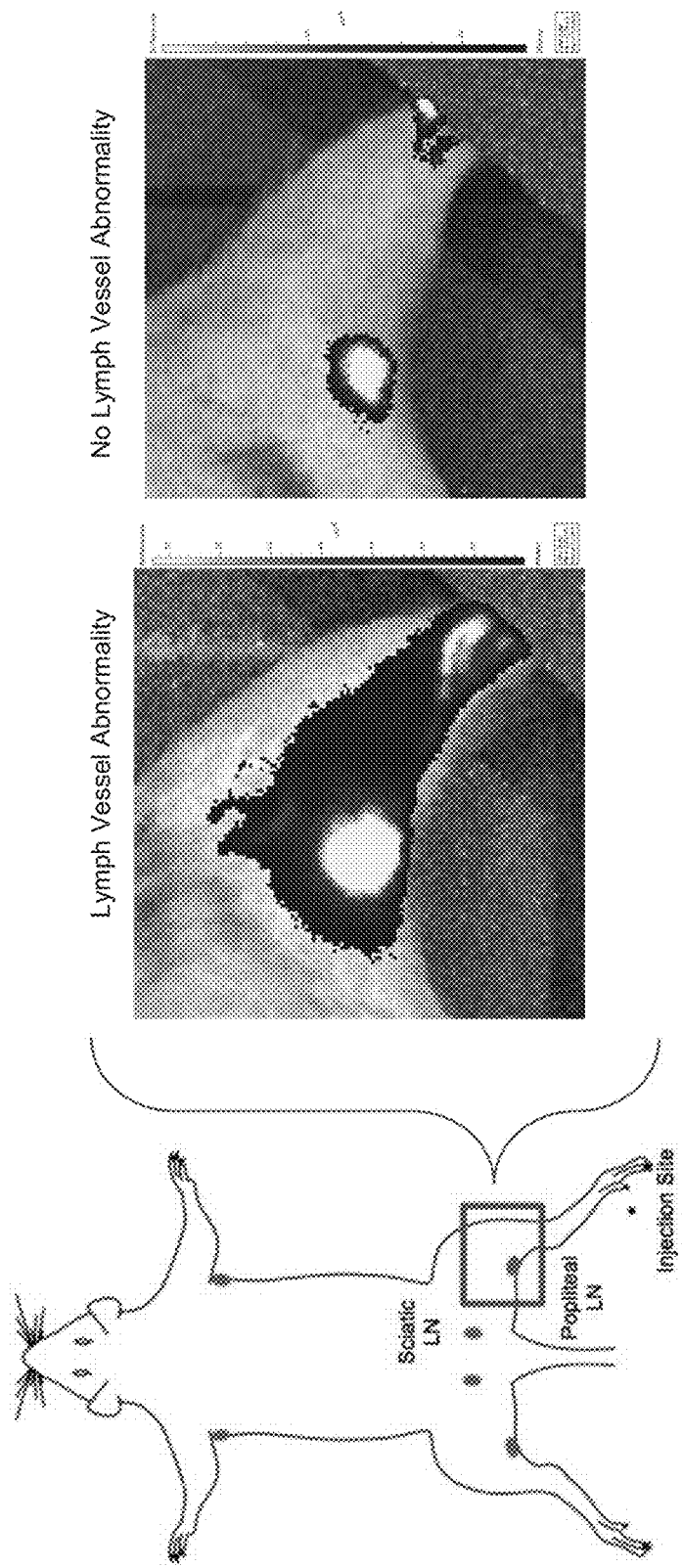
FIG. 20 depicts detection of lymphatic vessel abnormality through skin next to the popliteal LN of a mouse given ICG-LNP subcutaneously in the foot. It demonstrates the ability of ICG-LNP to detect lymphatic vessel abnormalities through the skin. The left image shows abnormal lymph vessels traveling above a mouse's right popliteal lymph node. In a normal mouse in the right image, no such vessel is detected. These observations were confirmed after removing the skin to image the lymphatic vessels from the skin underside.

The ICG-LNPs provided herein possess various advantageous properties make it superior to the ICG formulation known in the art, such as (1) rapid uptake into the lymphatics, following subcutaneous injection (see e.g., Table 5, FIG. 17), (2) rapid flow and widespread distribution throughout the lymphatic system (see e.g., FIGS. 9 and 10), (3) subsequent retention in the lymphatic vessels and lymph nodes upon first-pass through the lymphatic system (see e.g., FIG. 11), (4) excellent stability in vivo within the lymphatic system (see e.g., FIGS. 9-11), (5) stability in lymph node tissues, as shown by punctuated fluorescence seen under near-infrared microscopic imaging of lymph node tissue slices (see e.g., FIG. 11), (6) distribution into lymph node tissues, as shown in near-infrared microscopic imaging of lymph node tissue slices (see e.g., FIG. 11), (7) distinctive/enhanced high-resolution imaging of lymphatic vessels and lymph nodes with lipid-bound ICG compared to free ICG (see e.g., Table 2 and FIG. 10), (8) detection of downstream lymph nodes from the injection site that is not achievable with free ICG (Tables 2, 5, FIGS. 10, 17, 19), (9) extended duration of lymphatic vessel and LN imaging with lipid-bound ICG compared to free ICG (FIGS. 10, 19), (10) accumulation and trapping in lymph nodes, particularly those that are pathogenic (FIGS. 6, 8, 11, 19, 20), (11) detection of tumors with lymphatic vascularization (FIG. 4), (12) detection of sites of inflammation due to lymphangiogenesis and tertiary lymphoid organs (FIGS. 5-8), and (13) predominantly hepatic elimination via the bile duct into the intestine (FIG. 18).

A. Fluorescence Imaging Method

The contrast agent provided herein may also be used for a fluorescence imaging method. The fluorescence imaging method using the contrast agent according to this embodiment includes at least the steps of: administering the contrast agent to a subject or a sample obtained from the subject; irradiating the subject or the sample obtained from the subject with light; and measuring fluorescence from a substance derived from the particle present in the subject or in the sample obtained from the subject.

An example of the fluorescence imaging method using the contrast agent according to this embodiment is as described below. That is, the contrast agent according to this embodiment is administered to a specimen, or is added to a sample such as an organ obtained from the specimen. It should be noted that the specimen refers to all living organisms such as an experimental animal and a pet without any particular limitation. Examples of the specimen or the sample obtained from the specimen may include an organ, a tissue, a tissue section, a cell, and a cell lysate. After the administration or addition of the particle, the specimen or the like is irradiated with light in a near infrared wavelength region.

The imaging can be performed with a commercial fluorescence IVIS imaging apparatus (such as an IVIS Lumina Imaging System) and an ICG filter.

As described above, many photoimaging apparatuses are designed to use the wavelength range and the IVIS also corresponds to the absorption wavelength of an ICG monomer, i.e., 780 nm (excitation passband of a filter set 4: 705 to 780 nm).

In one aspect, the present invention provides a method for imaging a tissue or organ in a subject, comprising: administering to a subject in need of imaging a suitable amount of the ICG-LNPs, irradiating the subject with a light of suitable frequency, and obtaining an image of a tissue or organ of said subject by detecting the light emitted by the ICG. Nguyen, Q. T., and Tsien, R. Y. (2013) Fluorescence-guided surgery with live molecular navigation: A new cutting edge. Nat. Rev. 13, 653-662, the disclosure of which is incorporated by reference in its entirety.

In some embodiments, the method comprising: (1) administering to a subject, such as a human being, with a composition comprising the LNPs provided herein via subcutaneous, intradermal, intravenous, intramuscular, intratumoral, peritumoral injection; and (2) using near-infrared light/camera on endoscope or hand-held probe to detect fluorescence from ICG nanoparticles in tissues, therefor obtaining an image of the tissue or organ of the subject.

The imaging methods provided herein can be used in various applications, such as: (1) Lymph flow and drainage mapping, (2) Angiography, (3) Detection of lymphoid tissues, (4) Sentinel lymph node mapping, (5) Lymphatic vessel architecture abnormality detection, (6) Lymphatic metastatic cancer cell detection by altered lymph flow patterns or molecular targeting to cancer cells, and (7) Visualize delivery of drug contained in ICG nanoparticles (macroscopically and microscopically/histologically).

The ICG-LNP provided herein as a product is potent at only ~0.05 mg/kg ICG dose, or less, (as compared to FDA recommended intravenous dose: 0.5-2 mg/kg) (which is an ~10-fold lower dose due to 5-fold enhancement in intensity and a gain in pharmacokinetic stability).

In another aspect, the present invention provides a method to obtain an image of a tissue or organ of a subject, comprising administer the subject a dye, such as a NIR dye (e.g. ICG) at a dosage of less than about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, 0.02 mg/kg, or 0.01 mg/kg, dye (e.g., ICG) dose.

In some embodiments, the dose is between about 0.01 mg/kg to about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, or 0.02 mg/kg, inclusive, dye (e.g., ICG) dose.

In some embodiments, does is about 0.05 mg/kg to 0.5 mg/kg dye (e.g., ICG) dose, inclusive.

In some embodiments, the method comprises administering to a subject the ICG-LNP in an amount that is less than about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, 0.02 mg/kg, or 0.01 mg/kg ICG dose.

In some embodiments, the method comprises administering to a subject the ICG-LNP in an amount that is between about 0.01 mg/kg to about 0.5 mg/kg, 0.4 mg/kg, 0.3 mg/kg, 0.2 mg/kg, 0.1 mg/kg, 0.09 mg/kg, 0.08 mg/kg, 0.07 mg/kg, 0.06 mg/kg, 0.05 mg/kg, 0.04 mg/kg, 0.03 mg/kg, or 0.02 mg/kg, inclusive, ICG dose.

In some embodiments, the method comprises administering to a subject the ICG-LNP in an amount that is about 0.05 mg/kg to 0.5 mg/kg ICG dose, inclusive.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims.

EXAMPLES

The present invention is further exemplified, but not limited, by the following and Examples that illustrate the preparation of the compounds of the invention.

Example 1

Chemicals: Indocyanine green (ICG; $C_{43}H_{47}N_2NaO_6S_2$; sodium 2-[7-[3,3-dimethyl-1-(4-sulfonatobutyl)benz[e]indolin-2-ylidene]hepta-1,3,5-trien-1-yl]-3,3-dimethyl-1-(4-sulfonatobutyl)benz) was purchased from Sigma-Aldrich (St. Louis, Mo.). 1,2-distearoyl-sn-glycero-3-phosphocholine (DSPC), 1,2-distearoyl-sn-glycero-3-phosphoethanolamine-N-methoxy-polyethylene glycol-2000 (DSPEmPEG$_{2000}$), and L-a-phosphatidylcholine (Egg PC) were purchased from Avanti Polar Lipids (Alabaster, Ala.). Other reagents were analytical grade or higher.

Figure 3:
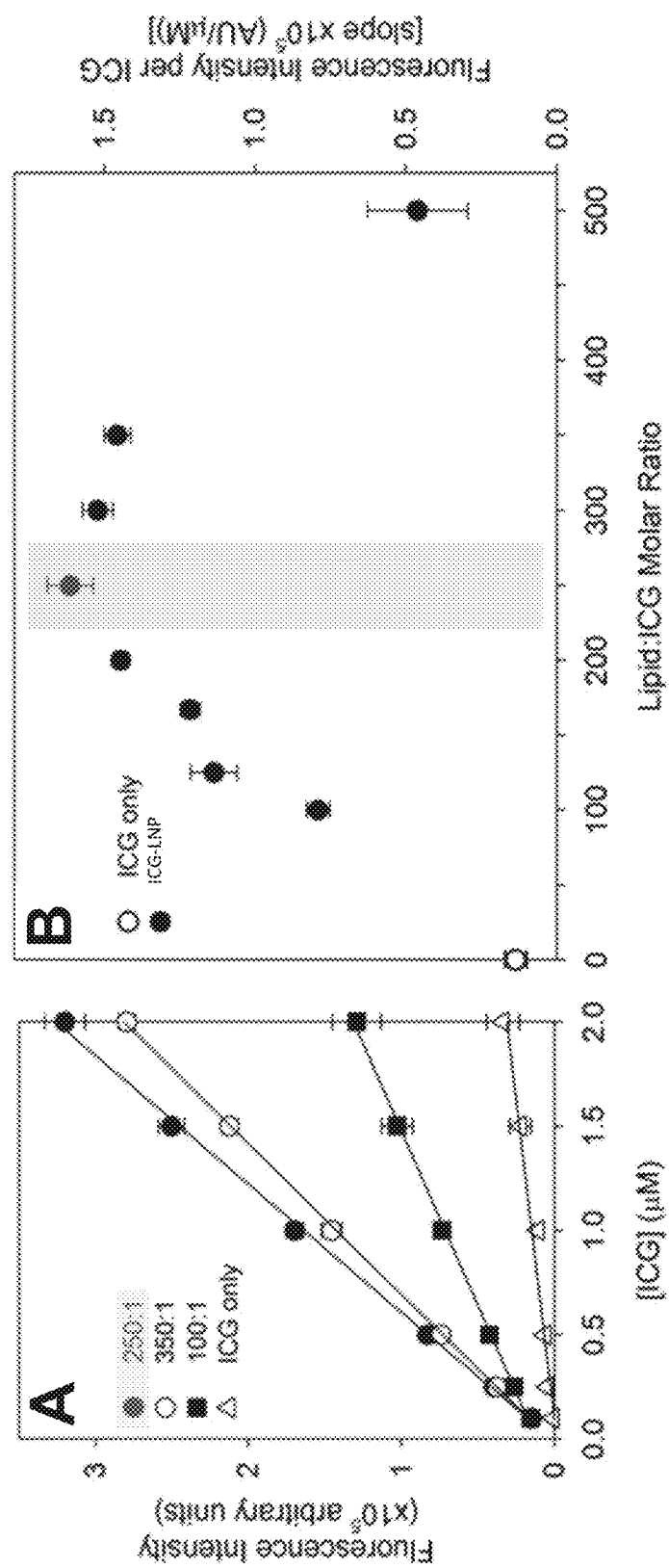
FIG. 3 depicts ICG-LNPs vs. free ICG fluorescence intensity and yield. (A) Effects of the lipid:ICG molar ratio on the ICG fluorescence yield (fluorescence intensity per micromolar ICG). ICG-LNPs with varying lipid:ICG molar ratios were prepared, and their fluorescence intensity per unit ICG was measured at the indicated concentrations. Only three of eight ICG-LNP formulations are presented for the sake of clarity; their data points are labeled according to their lipid:ICG molar ratios: (●) 250:1, (○) 350:1, and (■) 100:1 lipid:ICG molar ratios and (Δ) ICG only. Each fluorescence intensity data point is the mean±SD of eight replicates. (B) Effects of lipid:ICG molar ratio on fluorescence yield. The data from panel A were used to calculate the slope (fluorescence intensity per micromolar ICG) and plotted vs the lipid:ICG molar ratio: (○) free ICG only and (●) ICG-lipid nanoparticles (ICG-LNPs) at varying molar ratios. Each data point is the mean±SD of six replicates.
Figure 4:
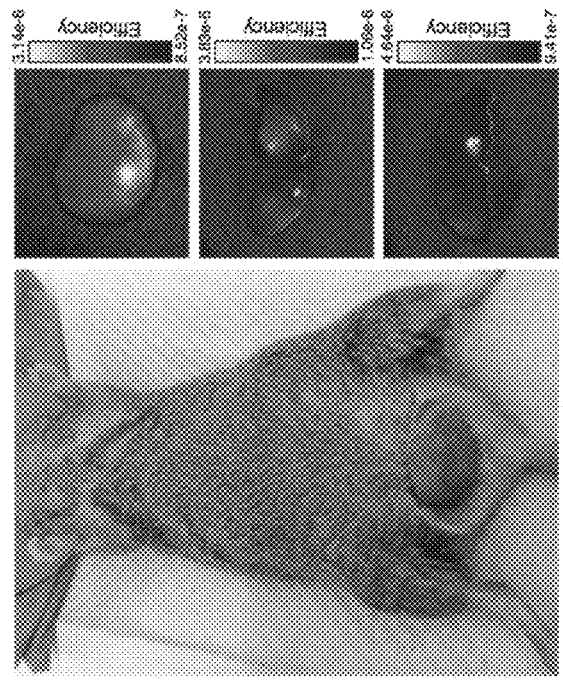
FIG. 4 depicts detection of tumors. Fluorescence intensity from ICG-LNPs in slices of excised tumors characterized by a licensed pathologist as malignant fibrosarcoma (top) and squamous cell carcinoma (bottom).
Figure 4:
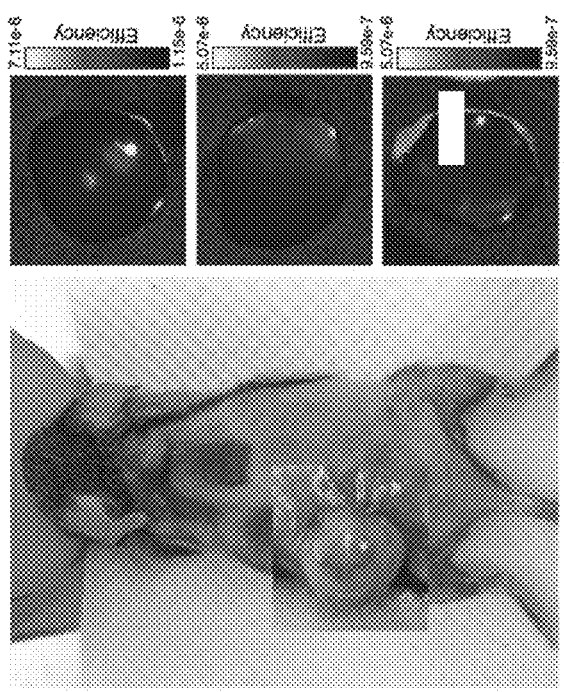
Figure 5:
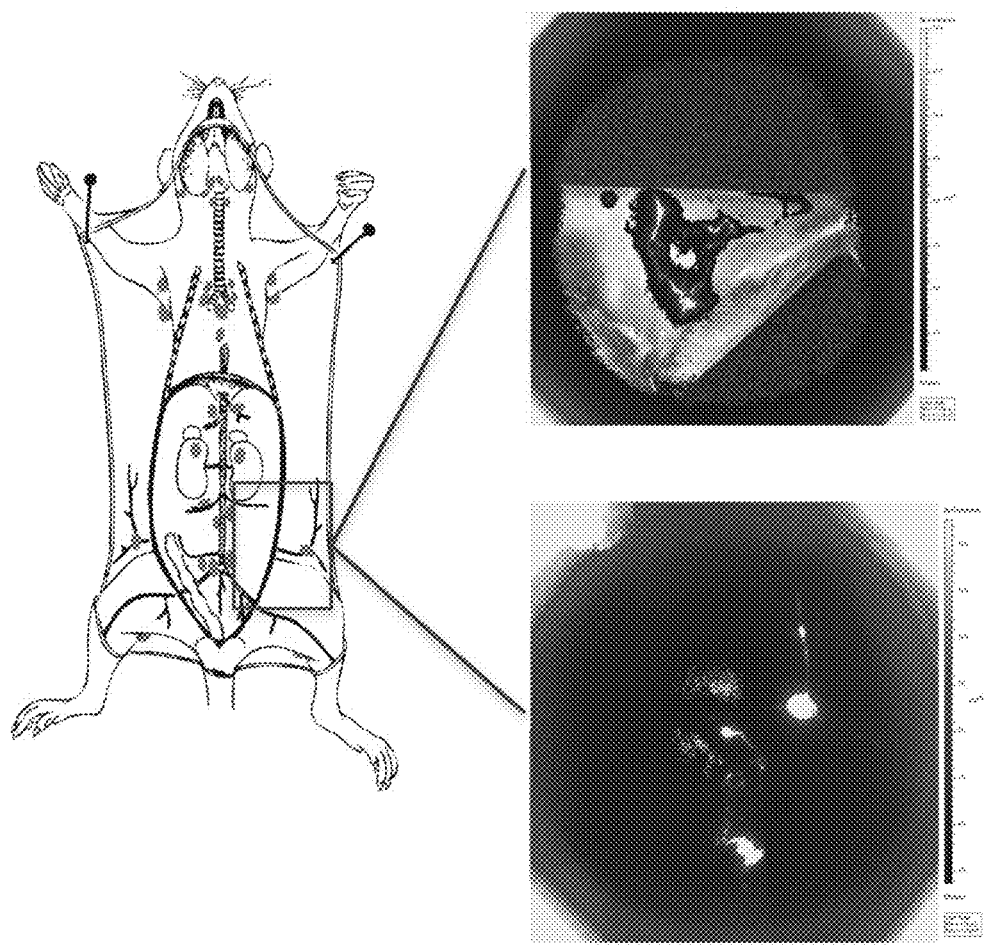
FIG. 5 depicts images from 2 different mice. Skin underneath left leg. Inflammation, lymphangiogenesis, and tertiary lymphoid organs detected in the skin of two streptozotocin (STZ) type 1 diabetic mice using ICG-LNPs.
Figure 6:
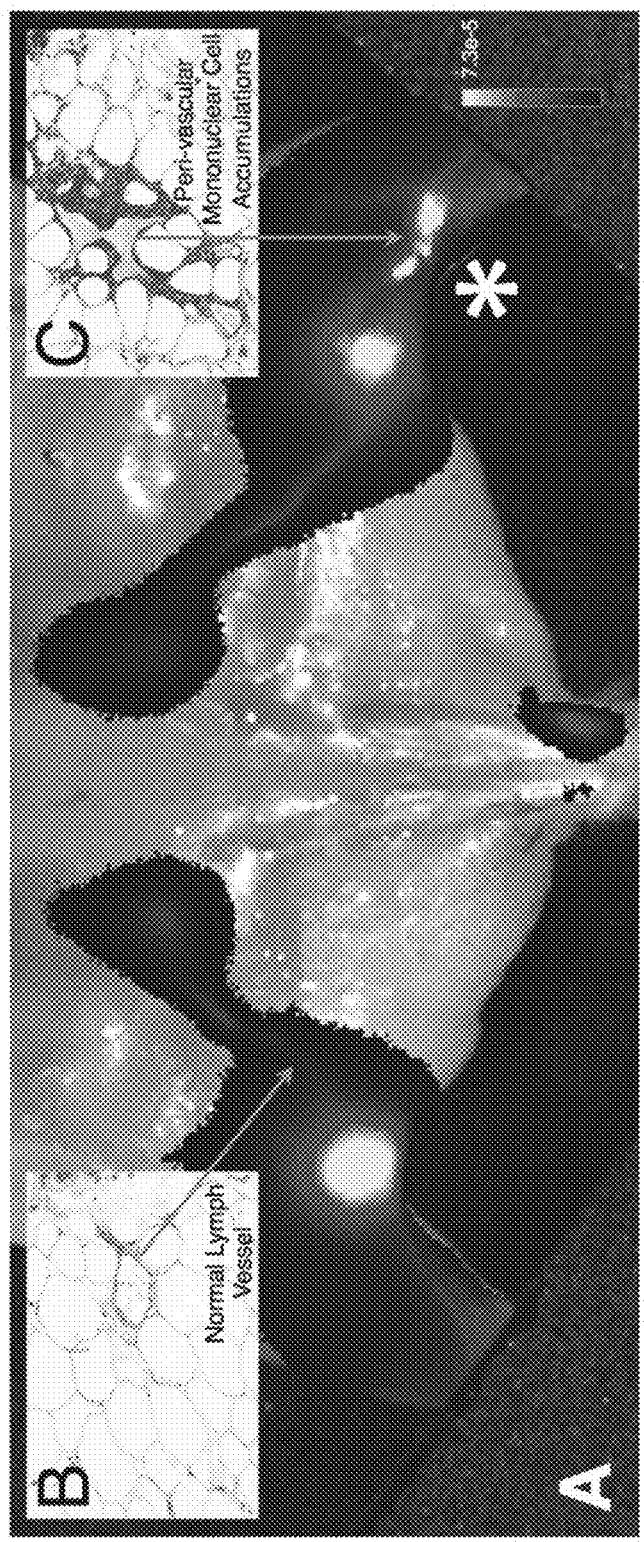
FIG. 6 depicts lymphatic abnormality with peri-vascular mononuclear cell (lymphocytes and histiocytes/macrophages) accumulations detected in the right leg of a mouse with ICG-LNPs. The mouse's skin is removed in this image.
Figure 7:
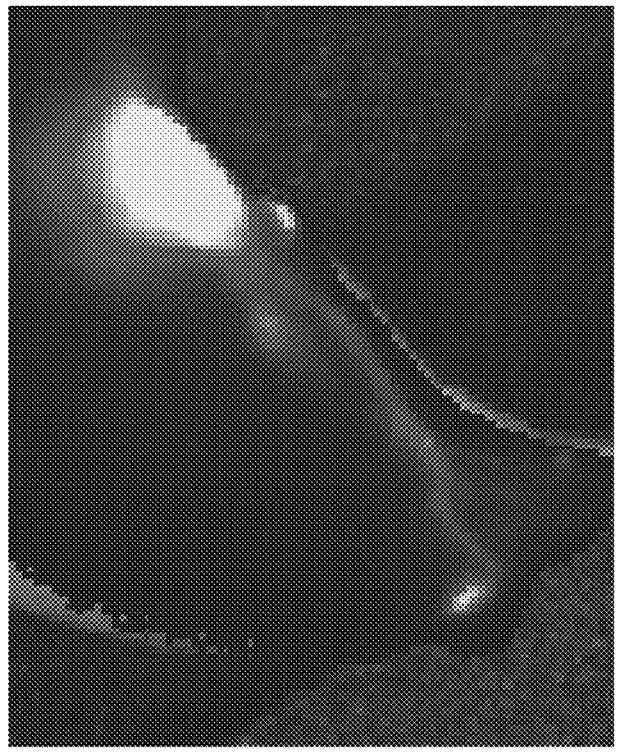
FIG. 7 depicts Lymphangiogenesis, lymph vessel dilation, and tertiary lymphoid organs in the left afferent lymph vessel of the left popliteal lymph node in a mouse detected with ICG-LNPs. The mouse's skin is removed in each of these images.
Figure 7:
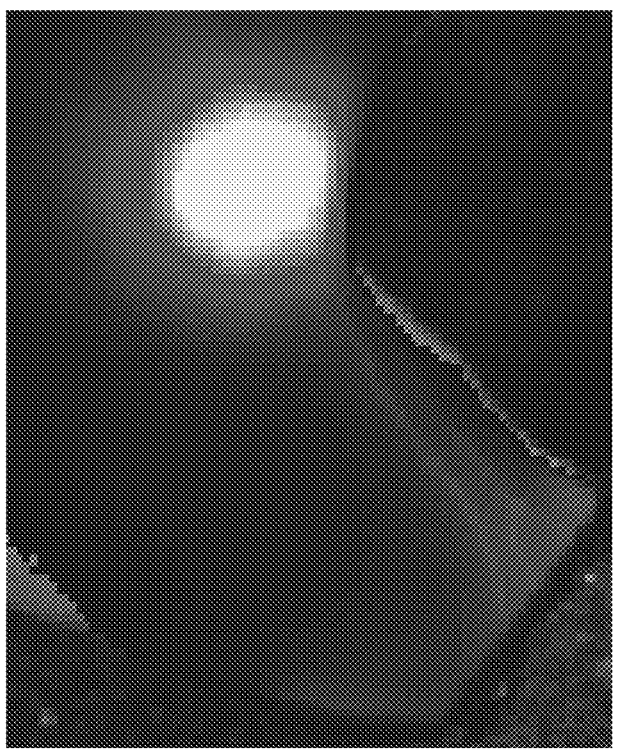

LNP Preparation. Control or empty LNPs and ICG-LNPs were prepared by thin film hydration and sonication. Briefly, DSPC dissolved in CHCl$_3$ and DSPEmPEG$_{2000}$ dissolved in CHCl$_3$:CH$_3$OH (3:1 v/v) were mixed (9:1 mol/mol) in a sterile test tube. The mixture was then dried under N$_2$ gas and reduced pressure into a thin film, which was vacuum desiccated overnight at room temperature. The thin film was rehydrated with 0.9% NaCl, 20 mM NaHCO$_3$ buffer at pH 7 (final lipid concentration of 20 mM) at 60° C. for 3 h. The LNP diameter was reduced to approximately 50-80 nm via a 15 min bath sonication at 55° C. For ICG-LNPs, ICG dissolved in 100% CH$_3$OH was added to the lipid mixture prior to it being dried into a thin film. ICG self-quenching (22) was reduced, and the density of ICG in the lipid membrane was optimized (FIG. 3). The mean diameters of LNPs and ICG-LNPs were obtained by particle size analysis with photon correlation spectroscopy (PCS) on a PSS-NICOMP 380 ZLS instrument (Particle Sizing Systems, Port Richey, Fla.). The ζ potential was measured on the same instrument. The ICG embedding efficiency was evaluated by separation of lipid-bound and free ICG by equilibrium dialysis. All experiments were performed under dark conditions, and light exposure was avoided.

90° Light Scattering of ICG Adsorbed to LNPs: ICG dissolved in 100% $CH_3OH$ was incubated with LNPs in plastic micronic tubes at lipid-ICG molar ratios of 25:1 to 500:1 for 20 minutes before diluting 25-fold with 0.9% NaCl, 20 mM $NaHCO_3$ buffered at pH 7 to minimize ICG-lipid interactions. Ninety degree light scattering was then measured on a Hitachi F-4500 fluorescence spectrophotometer (Troy, Mich.). The set parameters were $\lambda_{ex/em}$=660/660 nm and slit width$_{ex/em}$=2.5/5 nm. Samples were stored away from light at room temperature during observation.

Fluorescence. Fluorescence measurements were performed on a Victor3 V 1420-040 Multilabel Plate Reader (Perkin-Elmer, Waltham, Mass.) with a tungsten-halogen continuous wave lamp (75 W, spectral range of 320-800 nm) and excitation (769±41 nm) and emission (832±37 nm) filters (Semrock, Rochester, N.Y.) using 100µL of sample in flat bottom, untreated 96-well plates (Grenier Bio-one, Monroe, N.C.).

Light Exposure and Storage Stability. For light exposure stability (FIG. 13), samples of free ICG and ICG-LNPs at 2.0 µM ICG were exposed to overhead fluorescent tube lighting for 12 h. Fluorescence measurements were recorded at 0, 6, and 12 h. For storage stability (FIG. 12), samples were placed in the dark at 4° C. for up to 313 days. Fluorescence measurements were recorded at five different time points for free ICG and at 10 different time points for ICG-LNP. The time-dependent decay of ICG fluorescence was analyzed on the basis of an exponential decay model with GraphPad Prism version 6.0 (GraphPad Software, San Diego, Calif.). The data were expressed as t½ (half-life) and k (rate constant).

Tissue Depth Penetration. Cuboid chicken breast tissue phantoms of three different depths (0.5, 1.0, and 1.5 cm) were used to assess ICG fluorescence detection through tissue (FIG. 2). Tissue cuboids were placed over capillary tubes [70 µL capacity, 75 mm length, 1.2 mm inner diameter (Fisher Scientific, Hampton, N.H.)] filled with 50 µL of 30 µM free ICG or ICG-LNPs. White light and NIR images were captured within 15 min of the preparation of capillary tubes and tissue cuboids using a custom NIR charge-coupled device (CCD) camera built by Hamamatsu Photonics K.K. (Hamamatsu, Japan). Fluorescence intensity mean values of select areas, on a scale of 0 to 255 with 255 being the maximal brightness, were obtained with the analysis function in Adobe Photoshop CS4 (Adobe Systems Inc., San Jose, Calif.).

In Vivo NIR Lymphatic Imaging in Mice. Mice were kept under pathogen-free conditions, exposed to a 12 h light-dark cycle, and received food ad libitum prior to imaging. All procedures were approved by the University of Washington Institutional Animal Care and Use Committee.

Mice were anesthetized with 1.5% isoflurane, shaved to remove fur, and placed in a supine position on a 37° C. heat pad underneath an IVIS Lumina II NIR CCD camera (Perkin Elmer, Waltham, Mass.). Precontrast images were taken to confirm the absence of autofluorescence. Forty microliters of ICG-LNPs or free ICG was injected subcutaneously into the top of both rear feet. Immediately following injections, both feet were placed under gentle even pressure. Images were acquired for up to 120 min prior to euthanasia by cervical dislocation under anesthesia, upon which the skin was surgically opened to perform lymph node imaging.

Example 2

Lipid-ICG Interactions

To evaluate the interactions between ICG and lipid, empty (no ICG) LNPs were incubated with varying concentrations of ICG. If ICG molecules in solution bind to lipids in the membrane, it will cause LNPs to crosslink and aggregate, resulting in an increase in its apparent size detectable by a change in 90° light scattering and an increase in particle size. In a preliminary experiment. LNPs composed of egg-derived phosphatidylcholine (Egg PC) (containing mixed-length fatty acyl chains) exhibited an increase in light scattering intensity as ICG concentration was increased, indicating that ICG induced LNP aggregations. We next used LNPs with a well-defined phospholipid composition—DSPC containing two symmetrical C18 fatty acyl chains and DSPEmPEG$_{2000}$ (9:1 mol/mol)—to perform systematic studies. A fixed 10 mM lipid concentration in LNPs with varying ICG concentrations were allowed to interact for 20 min at 25° C.; the reaction was stopped by 25-fold dilution with buffered solution. The mixture was subjected to 90° light scattering analysis and photon correlation spectroscopy (PCS) to estimate particle size.

Figure 14:
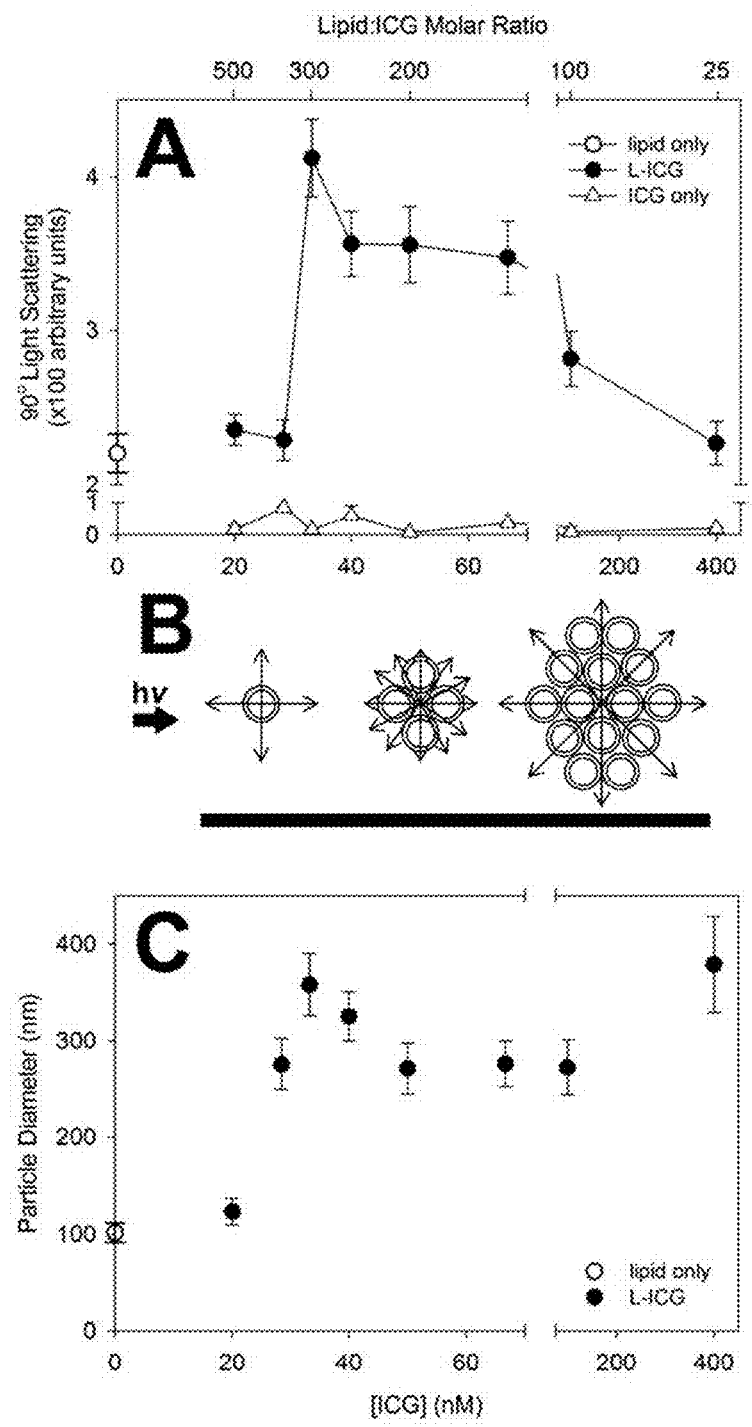
FIG. 14 depicts ICG concentration-dependent LNP aggregation and apparent size increase. Panel A: The effect of ICG concentrations on 90° light scattering intensity of LNPs. A fixed concentration of LNPs was incubated with varying ICG concentrations in a fixed volume. At 20 minutes, mixtures were diluted to stop the reaction and 90° light scattering intensity was measured with a fluorometer. Open circle symbol indicates empty lipid only nanoparticles, closed circle symbol indicates ICG lipid nanoparticle (ICG-LNP), and open triangle symbol indicates free ICG only. Each data point is the mean±SD often replicates. Panel B: Schematic drawing of light scattering efficiency detected by the photomultiplier tube (PMT; bold horizontal bar) 90° to the incident light (hv) path as LNPs aggregate and increase the particle size diameter. Panel C: The effect of ICG concentrations on particle size analysis by photon correlation spectroscopy of LNPs. Following collection of Panel A data, particle size analysis was performed. Open circle symbol indicates empty lipid only LNPs and closed circle symbol indicates ICG lipid nanoparticles (ICG-LNPs). Each data point is the mean±SD result from digital autocorrelation calculations following eight minutes of data collection.

Ninety degree light scattering intensity is expected to be low when particles are in single, non-aggregated form and increase with aggregation. However, when lipid aggregates become too large they may fall off the light path or electrons in a particle may not oscillate together in phase and cause intraparticle destructive interference, resulting in apparent decline of scattering intensity. As shown in FIG. 14A, empty LNPs (lipid only) have a low scattering intensity and free ICG (ICG only) has a consistent scattering intensity near zero regardless of the varying ICG concentration. When LNPs and ICG (ICG-LNPs) were mixed together, at low ICG concentrations (20-30 nM) a minimum light scattering intensity similar to the empty LNP control (lipid only) was detected. The scattering intensity of ICG-LNP increases approximately 1.5-fold when the ICG concentration increases from 30 to 70 nM (FIG. 14A). There is a minor decline in scattering intensity at 40 nM ICG, however, it is still significantly higher than at 20-30 nM ICG. At high concentrations (100-400 nM ICG), the scattering intensity declines as aggregates grow larger. FIG. 14B depicts a schematic drawing of the proposed aggregate formation that leads to an initial increase in light scattering intensity followed by a decrease in intensity as the particle size becomes exceedingly large. These data were confirmed by aggregate size analysis with PCS. As shown in FIG. 14C, at an initial ICG concentration of 20 nM, the particle diameter is similar to that of empty LNPs (~100 nm). The apparent ICG-LNP size increases about 2-fold at ICG concentrations of 20 to 100 nM. The apparent size fluctuates around 300 nm diameter at ICG concentrations between 30-100 nM, and then grows to about 400 nm at 400 nM ICG. In the region of 30-400 nM ICG, we detected a small population of smaller but distinct ICG-LNPs with consistent diameters of 60-90 nm (data not shown).

Collectively, these data indicate that ICG binds to lipid presented in empty pre-formed LNPs and leads to LNP aggregates, detected as apparent increase in particle size, and a discontinuous increase in light scattering intensity. Based on the lipid concentration of 10 mM and ICG concentrations 20-50 nM, these data give rise to a lipid-ICG molar ratio estimated to be between 200:1 to 500:1 that produces maximal lipid aggregation and apparent increase in particle size.

Impact of Lipid-ICG Interactions on ICG Fluorescence

Figure 15:
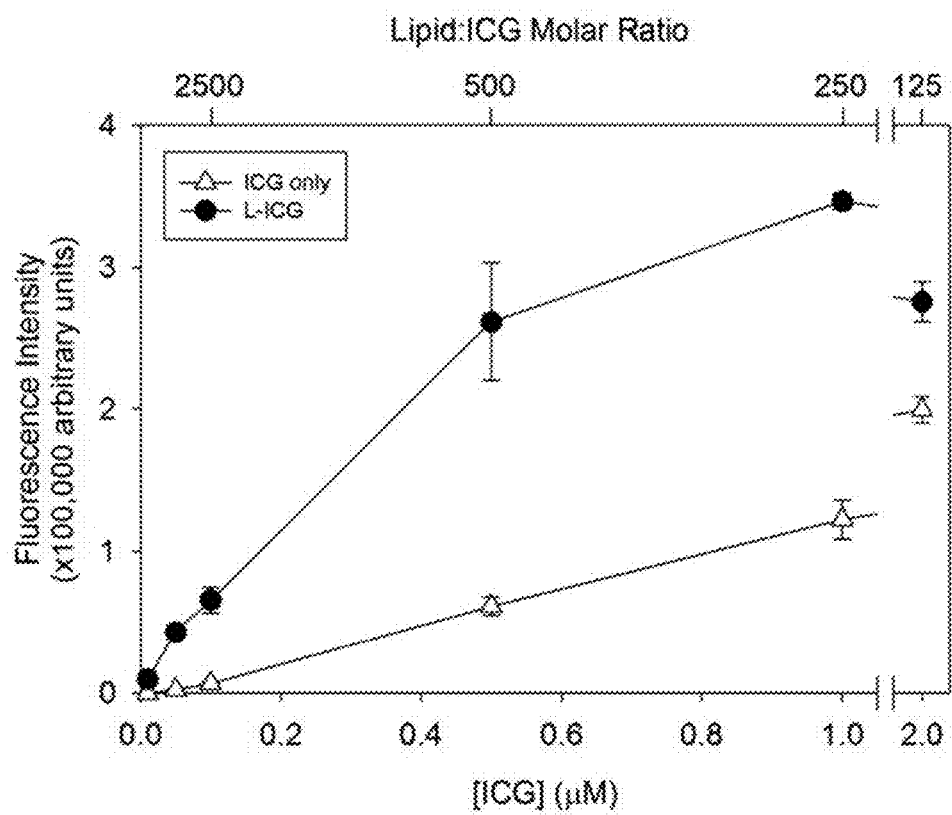
FIG. 15 depicts increased fluorescence intensity of ICG lipid nanoparticles (ICG-LNPs). A fixed concentration of LNPs was incubated with varying ICG concentrations in a fixed volume. At 20 minutes, mixtures were diluted 20-fold with buffered solution to stop the reaction and fluorescence intensity was measured with a fluorometer as described in the examples. Open triangle symbol indicates free ICG only and closed circle symbol indicates ICG lipid nanoparticles (ICG-LNPs). Each data point is the mean±SD of eight replicates.
Figure 16:
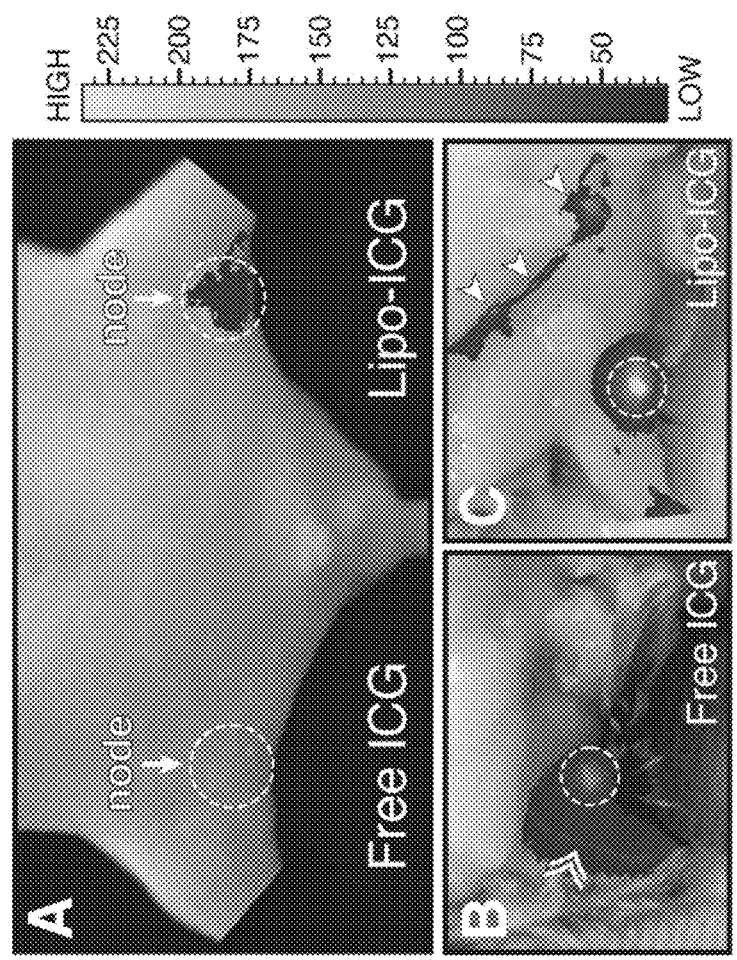
FIG. 16 depicts comparison of ICG lipid nanoparticles and free ICG NIR image behavior in mice after subcutaneous injection. Panel A: ICG lipid nanoparticles (ICG-LNP; left foot) or free ICG (right foot) were subcutaneously injected and NIR fluorescence image was collected at six minutes. Fluorescence image is overlaid on visual light photograph for anatomical representation. Dashed circle indicates the local popliteal node. Mouse is viewed in supine position. In another set of mice treated only with free ICG (Panel B) or ICG-LNP (Panel C) for six minutes, the skin was removed and analyzed further. Panel B: Visible light photograph is the image collected of the right leg of a mouse treated with free ICG in its right foot. Corresponding fluorescence image is overlaid. Double arrow (>>) indicates saphenous vein where free ICG appears to diffuse throughout the muscle tissue and the popliteal lymph node (dashed circle). Mouse is viewed in supine position. Panel C: Visible light photograph is the image collected of the right leg of a mouse treated with ICG-LNP in its right foot. Corresponding fluorescence image is overlaid. Dashed circle indicates popliteal lymph node and bold arrowheads indicate ventral pelvic and genital/regional lymph nodes. Mouse is viewed in supine position.
Figure 17:
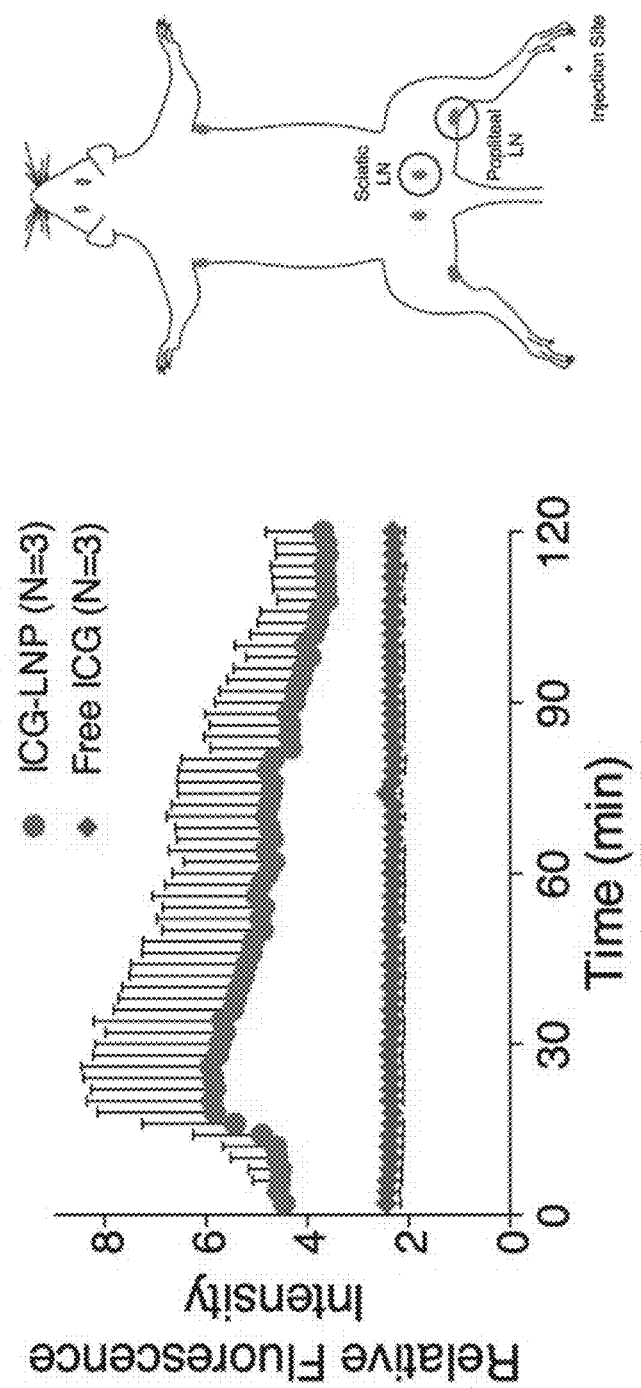
FIG. 17 depicts the pharmacokinetics of fluorescence intensity from free ICG vs. ICG-LNP in $2^{nd}$ draining lymph node (sciatic LN, ~2 cm from popliteal LN) detected through skin following subcutaneous administration in mouse foot. Mean±SEM. It shows the enhanced fluorescence intensity achieved with ICG-LNPs for visualizing the second downstream lymph node (sciatic LN) from the injection site. The intensity with ICG-LNP is 2-fold to 3-fold higher than that achieved with free ICG. There is also clear distribution and elimination characteristics detected with only ICG-LNPs and not free ICG.

We next determined the impact on fluorescence intensity due to ICG binding to lipid. We used the lipid-ICG molar ratio range of 125:1 to 25,000:1. Due to the self-quenching property of ICG, the reaction mixture was diluted 20-fold with buffered solution to the linear ICG concentration range of 0.01-2.0 mM. As shown in FIG. 15, the presence of lipid in the mixture increases the fluorescence intensity of ICG at equivalent ICG concentrations. As ICG concentration increases from 0.01 to 1.0 mM, the fluorescence intensity progressively widens for the mixture containing lipid vs. control. At 0.1, 0.5, and 1.0 mM ICG, fluorescence intensity increased by 10.0-fold (65,720 vs. 6,600), 4.3-fold (261,640 vs. 61.360), and 2.8-fold (346,610 vs. 122,530), respectively. At 2.0 mM ICG, the lipid-mediated enhancement in ICG fluorescence intensity was less and only a 1.4-fold increase (275,820 vs. 199,420) was observed. At a fixed 250 µM lipid concentration and 0.5, 1.0, and 2.0 µM ICG, the equivalent lipid-ICG molar ratios for these values are 500:1, 250:1, and 125:1, respectively (FIG. 15). Therefore, the optimal lipid-ICG molar ratio that exhibits the highest fluorescence intensity is estimated to be 125:1 to 500:1. This estimate is consistent with data collected from 90° light scattering and PCS size analysis. These values, derived from ICG and pre-formed LNP interactions, were used as the target range for subsequent ICG-LNP preparation and characterization studies.

Incorporation of ICG into LNPs to Stabilize and Maximize ICG Fluorescence

Instead of adding ICG in solution to lipid as admixtures in buffered solution, we mixed ICG and lipid together in an organic solution, first, then removed the solvent and rehydrated in buffer to form LNPs inserted or embedded with ICG. ICG has a significant overlap in absorption and emission spectra (data not shown) and consequently exhibits self-quenching potential at high concentrations. Thus, we made LNPs embedded or incorporated with different concentrations (densities) of ICG embedded into the lipid. If ICG density is too high, the close proximity between ICG molecules may induce self-quenching due to concentration-dependent molecular interactions. Moreover, ICG incorporated into lipid without exposure to water would provide higher fluorescence than ICG molecules exposed to water, which quenches ICG fluorescence. Eight lipid-ICG molar ratios ranging from 100:1 to 500:1 were evaluated. FIG. 3A represents the fluorescence intensity per unit of ICG slope at typical ICG concentrations for three lipid-bound ICG samples (equivalent to 100:1, 250:1, and 350:1 mol/mol) and a soluble ICG control. At 0.01-2.0 mM ICG, the fluorescence intensity appears to increase linearly. Note that the slope of the 250:1 line is the steepest, followed by 350:1, 100:1, and ICG only. To determine the optimum lipid-ICG molar ratio, we evaluated the slope of the line for each formulation (for clarity, only three of eight total lines are presented in FIG. 3A).

The slope equals fluorescence intensity per µM ICG. As shown in FIG. 3B, due to a reduction in ICG density and self-quenching, the fluorescence intensity per ICG (slope) increases as the lipid-ICG molar ratio increases from 100:1 to 250:1, at which point the maximum is reached. The fluorescence intensity per ICG then decreases at 300:1 and 350:1, followed by a significant decrease at 500:1. Thus, we observed the peak fluorescence intensity per ICG at lipid-ICG molar ratio 250:1.

As the 250:1 lipid-ICG molar ratio exhibits the highest fluorescence intensity per ICG, we characterized the 250:1 formulation using particle size analysis by photon correlation spectroscopy (PCS) and particle surface charge (zeta potential) analysis by electrophoretic light scattering (ELS). The 250:1 formulation consisted of a monodisperse population of particles with a 56.8±4.4 nm diameter and a −33.1±3.1 mV zeta potential. Equilibrium dialysis indicated the ICG incorporation efficiency was 97.8±0.6%. Due to reproducible and almost complete incorporation of ICG, this formulation was selected without further purification for subsequent in vitro and in vivo studies.

Effects of Lipid Incorporation on Enhancing ICG Stability for Light Exposure and Storage We next evaluated the stability of ICG-LNP in 4° C. storage and under light exposure to simulate the environment in clinical settings. As shown in FIG. 13, the fluorescence intensity of ICG-LNP decreases to 87.6±0.5% of the initial value after 6 hours of light exposure and experiences no further decrease after 12 hours ($t_{1/2}$=67.5±11.8 h, k=0.011±0.002 $h^{-1}$). In contrast, the fluorescence intensity of free ICG in solution drops to 2.5±0.5% of its initial value after 6 hours of light exposure ($t_{1/2}$=0.036±0.005 h, k=19.2±2.7 $h^{-1}$), indicating the light instability of ICG in aqueous solutions.

To evaluate longer-term storage stability, we kept ICG-LNP in the dark at 4° C. and measured the fluorescence intensity multiple times over 313 days. As shown in FIG. 12 and Table 1, about 78.2±2.8% of the initial fluorescence intensity was recorded after eight months of storing ICG-LNP ($t_{1/2}$=394 days [95% CI: 360, 434], k=1.76×$10^{-3}$ $days^{-1}$ [95% CI: 1.60×$10^{-3}$, 1.93×$10^{-3}$]). However, for free ICG in buffer, only 0.3±0.2% of the initial ICG fluorescence was observed after eight months of storage ($t_{1/2}$=1.19 days [95% CI: 1.14, 1.25], k=582×$10^{-3}$ $days^{-1}$ [95% CI: 554× $10^{-3}$, 609×$10^{-3}$]).

TABLE 1

| Storage stability kinetics.[a] | | | |
|---|---|---|---|
| | % ICG fluorescence[b] (8 months) | $T_{1/2}$ (days) | $T_{1/2}$ (×$10^{-3}$ $day^{-1}$) |
| ICG-lipid nanoparticle | 78.2 +/− 2.8 | 394 (360, 434) | 1.76 (1.60, 1.93) |
| Free ICG | 0.3 +/− 0.2 | 1.19 (1.14, 1.25) | 582 (554, 609) |

[a]Stored in the dark at 4° C.
[b]Mean ± SD of samples (N = 2 each) stored for 8 months.
[c]t½ (95% CI) and k (95% CI) calculated from multiple time points (N = 10) over 313 days.
[d]t½ (95% CI) and k (95% CI) calculated from multiple time points (N = 5) over 239 days.

Enhanced NIR Imaging of ICG-LNPs In Vitro

To compare fluorescence signal intensity between ICG-LNP (250:1 lipid-ICG molar ratio formulation) and free ICG, we prepared chicken breast cuboids with increasing muscle tissue thicknesses of 0.5, 1.0, and 1.5 cm (FIG. 2F). We filled all capillary tubes (75 mm in length, 1.2 mm inner diameter) with 50 mL of 30 mM ICG (1.5 nmol ICG) (FIG. 2B). As shown in FIG. 2A, the intensity of the capillary tube filled with ICG-LNP is 3.2-fold higher than that of free ICG (intensity mean=111.7 vs. 34.5, respectively). When placed under three tissue cuboids, with increasing depth from left to right, free ICG fluorescence (top three cuboids) was only detectable across 0.5 cm depth (top left cuboid; intensity mean=9.0) but not through thicker depths; ICG-LNP fluorescence (bottom three cuboids) was detectable across 0.5 cm, 1.0 cm, and 1.5 cm depths (intensity mean=112.1, 77.3, 10.0, respectively) (FIG. 2C). Further analysis indicates that only ICG-LNP in capillary tubes can be detected across 1.5 cm of muscle tissue (intensity mean for 0.5, 1.0, 1.5 cm depths=100.9, 68.0, 15.2, respectively) (FIGS. 2E and 2F).

Effects of ICG-LNP on NIR Lymphatic Image Resolution in Mice

With the stable and optimized ICG-LNP formulation, we performed in vivo proof of principle optical imaging experiments in mice. To compare free versus ICG-LNP, we subcutaneously administered ICG in 40 mL (0.5 nmol of ICG), either in free or LNP-bound form, to the mouse's left or right foot (FIG. 16A). At six minutes, only the foot that received ICG-LNP (but not free ICG) exhibited a detectable popliteal node through the skin (FIG. 16A). Only when the image was collected below the skin, both popliteal lymph nodes became detectable. The ICG intensity mean of the popliteal lymph node that received free ICG was 37.0 compared to 208.1 for that treated with ICG-LNP (data not shown). To further compare the lymphatic image resolution of free ICG versus ICG-LNP, in another set of mice, we administered ICG to both feet either in free or LNP form with the same dose. As shown in FIG. 16B, at six minutes post administration and after removal of the skin, the animal receiving free ICG showed diffusion of ICG into the blood (saphenous vein). In this case, ICG was clearly detectable in the local popliteal node (FIG. 16B). In contrast, in the mouse treated with ICG-LNP, not only the popliteal lymph node intensity is much higher, but also a lymphatic track leading to ventral pelvic and genital/regional nodes is readily visible (FIG. 16C). Distribution of free ICG to this lymphatic track was not observed.

Lymphatic Mapping and Sentinel Lymph Node Detection

Table 2 shows the fluorescence intensity detected from ICG-LNP and free ICG in downstream lymph nodes and vessels from the subcutaneous injection site in a mouse foot (popliteal afferent vessel>popliteal LN>popliteal efferent vessel>sciatic>medial iliac>gastric>axillary). The intensity detected from ICG-LNP was greater in all cases than that from free ICG. In addition, higher resolution was achieved with ICG-LNP as a higher number of lymph nodes were detected with ICG-LNP compared to free ICG. This demonstrates the increased intensity and high-resolution of ICG-LNPs over that of free ICG.

dose required for free ICG due to the unique ICG stabilization and fluorescence intensity amplification permitted by our lipid nanoparticles.

TABLE 3

Typical indocyanine green (ICG) subcutaneous dose quantities for in vivo lymphatic imaging with ICG-LNPs vs. free ICG.

| | ICG-LNP Subcutaneous Dose | Free ICG Subcutaneous Dose |
|---|---|---|
| µg/kg | 0.097 µg/kg | 1.25 µg/kg |
| Ref. | N/A | Sevick-Muraca EM (2012) Ann Rev Med, 63: 217. |

Table 4 shows that equal doses of ICG exhibit different in vivo pharmacokinetic behavior depending on if ICG is in free or lipid nanoparticle form. ICG-LNP allows 1.4 to nearly 2-fold higher fluorescence intensity exposure, maximum intensity, and a more rapid rate of elimination. These properties support the amplified fluorescence intensity achieved in vivo with ICG-LNPs.

TABLE 4

In vivo pharmacokinetics of fluorescence intensity from free ICG vs. ICG-LNP in $1^{st}$ draining lymph node (popliteal LN) detected through skin following subcutaneous administration in mouse foot.

| | Free ICG (N = 3) | ICG-LNP (N = 3) | ICG-LNP/Free ICG Ratio |
|---|---|---|---|
| $AUC_{0-2\ hr}$ (a.u.*min) | 61.65 ± 34.83 | 87.63 ± 16.43 | 1.42 |
| $Intensity_{max}$ (a.u.) | 0.66 ± 0.42 | 1.25 ± 0.15 | 1.89 |
| k ($hr^{-1}$) | 0.19 ± 0.17 | 0.32 ± 0.09 | 1.68 |

*Fluorescence intensity = arbitrary units (a.u.)

Table 5 shows the fluorescence intensity achieved over time in the $1^{st}$ and $2^{nd}$ draining lymph nodes (popliteal and sciatic, respectively) from the subcutaneous injection site in the mouse foot. Following 2 hours, signal in the $1^{st}$ draining

TABLE 2

In vivo fluorescence intensity from select lymph nodes and vessels in mice following subcutaneous injection of free ICG vs. ICG-LNP

| Lymph Node (LN) or vessel | ICG-lipid nanoparticles max NIRF intensity[a] ($10^{-5}$ a.u.) | No. of nodes detected | Free TCG max NIRF intensity[a] ($10^{-5}$ a.u.) | No. of nodes detected | ICG-LNP/free ICG max NIRF intensity ratio |
|---|---|---|---|---|---|
| Axillary* | 1.7 ± 0.2 | 2 | 0.8 ± 0.1 | 2 | 2.1 |
| Gastric | 11.6 ± 3.2 | 4 | 2.5 ± 1.3 | 1-2 | 4.6 |
| Medial iliac* | 13.1 ± 2.1 | 2 | 4.1 ± 1.6 | 1-2 | 3.2 |
| Sciatic* | 5.4 ± 1.5 | 1 | 0.6 ± 0.1 | 0 | 9.0 |
| Pop efferent | 7.9 ± 2.6 | NA | 0.6 ± 0.1 | NA | 13.2 |
| Pop afferent* | 5.2 ± 1.4 | NA | 0.6 ± 0.2 | NA | 8.7 |
| Popliteal (Pop) | 38.4 ± 13.6 | 1 | 4.7 ± 2.2 | 1 | 8.2 |

[a]Maximum near-infrared fluorescence (NIRF) intensity (arbitrary units, a.u.) detected at respective lymph node or vessel.
Mean ± SEM (N = 3-4).
NA, not applicable.
*P-value <0.05.

Table 3 shows the dose of ICG in ICG-LNP form is 8% of the typical dose used for subcutaneous administration of free ICG. The ICG dose in lipid nanoparticles is <10% of the lymph node decreases approximately by half. Signal in the $2^{nd}$ draining lymph node (which is approximately 70% of that in the $1^{st}$ lymph node) decrease by approximately 25%.

This indicates the ability to assess lymph node function of initial and downstream draining lymph nodes in vivo using ICG-LNPs.

TABLE 5

In vivo fluorescence intensity through skin from mouse lymph nodes following subcutaneous injection of ICG-LNP.

| | ICG-LNP (N = 3) Relative Fluorescence Intensity | |
|---|---|---|
| | t = 0 min | t = 2 hr |
| $1^{st}$ Draining LN (Popliteal LN) | 1.25 ± 0.15 | 0.61 ± 0.16 |
| $2^{nd}$ Draining LN ~2 cm from $1^{st}$ (Sciatic LN) | 0.88 ± 0.22 | 0.66 ± 0.18 |

* Fluorescence intensity = arbitrary units (a.u.)

Example 3

Tumor sentinel lymph node detection/mapping. Perform one to ten deep pertumoral injections and one to ten subcutaneous pertumoral injections. For each injection, administer 0.01-10 mL of 0.1-100 µM ICG in ICG-LNPs. Massage injection site for approximately 5 minutes. Perform lymphatic mapping using a handheld, head-mounted, or otherwise positioned near-infrared imaging system.

Lymphatic function and lymphatic system characterization in healthy individuals or diabetic, cancer, or other disease patients. In healthy or diseased individuals, perform one to ten subcutaneous injections at any location in the body. For each injection, administer 0.01-10 mL of 0.1-100 µM ICG in ICG-LNPs. Massage injection site for approximately 5 minutes. Perform lymphatic mapping/imaging/recording using a handheld, head-mounted, or otherwise positioned near-infrared imaging system. Assess changes in lymph vessel (LV) architecture, LV permeability or leakiness, LV diameter, LV density, lymph flow and other lymphatic kinetic parameters, lymph node (LN) morphology or size, LN permeability or leakiness, LN localization, among other functional, phenotypic, or descriptive characteristics. In patients using the fluorescent signal detected from the lymphatics, take a ratio of "disease signal":"normal signal" to calculate an index to characterize the lymphatic differences between diseased and healthy individuals.

Endoscopic detection of lymphatic vessels and nodes in intestine, blood, and lymph vessels. Using endoscope with a hyperdermic needle and near-infrared imaging capability, inject into the intestinal epithelium or into a blood or lymph vessel endothelium 0.01-10 mL of 0.1-100 µM ICG in ICG-LNPs. Perform lymphatic mapping using an endoscopic near-infrared imaging system.

Abnormal liver function detection. Perform intravenous bolus injection or infusion of 0.01-100 mL of 0.1-100 µM ICG in ICG-LNPs. Image fluorescence signal from liver using a handheld, head-mounted, or otherwise positioned near-infrared imaging system. Measure the terminal half-life of the fluorescence signal from the liver. Compare the terminal half-life to normal healthy controls to assess any liver dysfunction.

Routes of metastatic cancer spread detection. Perform one to ten subcutaneous, intratumoral, or peritumoral injections. For each injection, administer 0.01-10 mL of 0.1-100 µM ICG in ICG-LNPs. Massage injection site for approximately 5 minutes if the injection site is palpable. Perform lymphatic mapping using a handheld, head-mounted, endoscopic, laporoscopic, or otherwise positioned near-infrared imaging system. Assess enlargement of lymph vessels and nodes, vessel clogging or leakage, or other characteristics associated with metastatic spread of cancer cells.

Blood vessel and cardiovascular pathology detection. Perform intravenous bolus injection or infusion of 0.01-100 mL of 0.1-100 µM ICG in ICG-LNPs. Image fluorescence signal from blood vessels or pathological lesions using endoscopic, handheald, head-mounted, or otherwise positioned near-infrared imaging system to assess differences between normal and blood vessel and cardivascular pathologies.

REFERENCES

1. Nguyen Q T & Tsien R Y (2013) Fluorescence-guided surgery with live molecular navigation—a new cutting edge. *Nature reviews* 13(9):653-662.
2. Baker K J (1966) Binding of sulfobromophthalein (BSP) sodium and indocyanine green (ICG) by plasma alpha-1 lipoproteins. *Proceedings of the Society for Experimental Biology and Medicine. Society for Experimental Biology and Medicine* (New York, N.Y 122(4):957-963.
3. Mordon S, Devoisselle J M, Soulie-Begu S, & Desmettre T (1998) Indocyanine green: physicochemical factors affecting its fluorescence in vivo. *Microvascular research* 55(2):146-152.
4. Saxena V, Sadoqi M, & Shao J (2003) Degradation kinetics of indocyanine green in aqueous solution. *Journal of pharmaceutical sciences* 92(10):2090-2097.
5. Zhou J F. Chin M P, & Schafer S A (1994) Aggregation and degradation of indocyanine green. *SPIE Proc. Laser Surg.: Adv. Charact., Ther., Syst. IV* (2128):495-505.
6. Kraft J C, Freeling J P, Wang Z, & Ho R J (2014) Emerging research and clinical development trends of liposome and lipid nanoparticle drug delivery systems. *Journal of pharmaceutical sciences* 103(1):29-52.
7. Daemen T, et al. (1997) Different intrahepatic distribution of phosphatidylglycerol and phosphatidylserine liposomes in the rat. *Hepatology* 26(2):416-423.
8. Jeong H S, et al. (2013) The effect of mannosylation of liposome-encapsulated indocyanine green on imaging of sentinel lymph node. *Journal ofliposome research.*
9. Proulx S T, et al. (2010) Quantitative imaging of lymphatic function with liposomal indocyanine green. *Cancer research* 70(18):7053-7062.
10. Turner D C, Moshkelani D, Shemesh C S, Luc D, & Zhang H (2012) Near-infrared image-guided delivery and controlled release using optimized thermosensitive liposomes. *Pharmaceutical research* 29(8):2092-2103.
11. Zhuang Y, et al. (2012) PEGylated cationic liposomes robustly augment vaccine-induced immune responses: Role of lymphatic trafficking and biodistribution. *J Control Release* 159(1):135-142.
12. Suganami A, et al. (2012) Preparation and characterization of phospholipid-conjugated indocyanine green as a near-infrared probe. *Bioorganic & medicinal chemistry letters* 22(24):7481-7485.
13. Kraft J C & Ho R J (2014) Interactions of indocyanine green and lipid in enhancing near-infrared fluorescence properties: the basis for near-infrared imaging in vivo. *Biochemistry* 53(8):1275-1283.
14. Hua J, et al. (2012) In vivo imaging of choroidal angiogenesis using fluorescence-labeled cationic liposomes. *Molecular vision* 18:1045-1054.

15. Li X, et al. (1995) Tumor localization using fluorescence of indocyanine green (ICG) in a rat model. *Proc. SPIE* 2389:789-797.
16. Philip R, Penzkofer A, Baumler W, Szeimies R M, & Abels C (1996) Absorption and fluorescence spectroscopic investigation of indocyanine green. *J. Photochem. Photobiol. A: Biol.* 96:137-148.
17. Rajagopalan R, Uetrecht P, Bugaj J E, Achilefu S A, & Dorshow R B (2000) Stabilization of the optical tracer agent indocyanine green using noncovalent interactions. *Photochemistry and photobiology* 71(3):347-350.
18. Engel E, et al. (2008) Light-induced decomposition of indocyanine green. *Investigative ophthalmology & visual science* 49(5): 1777-1783.
19. Holzer W, et al. (1998) Photostability and thermal stability of indocyanine green. *Journal of photochemistry and photobiology* 47(2-3): 155-164.
20. Sandanaraj B S, Gremlich H U, Kneuer R, Dawson J, & Wacha S (2010) Fluorescent nanoprobes as a biomarker for increased vascular permeability: implications in diagnosis and treatment of cancer and inflammation. *Bioconjugate chemistry* 21(1):93-101.
21. Proulx S T, et al. (2013) Use of a PEG-conjugated bright near-infrared dye for functional imaging of rerouting of tumor lymphatic drainage after sentinel lymph node metastasis. *Biomaterials* 34(21):5128-5137.
22. MacDonald R I (1990) Characteristics of self-quenching of the fluorescence of lipid-conjugated rhodamine in membranes. *The Journal of biological chemistry* 265(23): 13533-13539.

The invention claimed is:

1. A composition, comprising:
    (i) a lipid nanoparticle comprising a lipid membrane; and
    (ii) a plurality of indocyanine green (ICG) molecules, wherein at least 95% of said ICG molecules are embedded in said lipid membrane, wherein said nanoparticle has an average size of 50 nm to 100 nm.
2. The composition of claim 1, wherein said lipid membrane comprises 1,2-Distearoyl-sn-glycero-3-phosphocholine (DSPC), and 1,2-distearoyl-sn-glycero-3-phosphoethanolamine-N-methoxy-polyethylene glycol-2000 (DSPEmPEG2000).
3. The composition of claim 1, wherein at least 99% of said ICG is embedded in said lipid membrane.
4. The composition of claim 1, wherein substantially 100% of said ICG is embedded in said lipid membrane.
5. The composition of claim 1, wherein said lipid nanoparticle is suspended in a biocompatible buffer that has a pH 5-8 and Osm ~303 mOSM.
6. The composition of claim 1, wherein said nanoparticle has an average size of 50 nm to 80 nm.
7. The composition of claim 1, wherein said nanoparticle has a negative surface charge.
8. The composition of claim 1, wherein said nanoparticle is stable in serum with between 90%, to 100% of its initial fluorescence retained in heat-inactivated-serum after 6 h, at 25° C.
9. The composition of claim 1, wherein said nanoparticle has a fluorescence intensity between 4- and 5-fold higher than that of free ICG in aqueous solution.
10. The composition of claim 1, wherein said nanoparticle has a fluorescence intensity between 4- and 100,000-fold higher than that of free ICG in aqueous solution after being stored at 4° C for between 0 and 300 days.
11. The composition of claim 1, wherein said composition is potent at less than 0.5 mg/kg body weight ICG dose.
12. The composition of claim 1, wherein said composition is potent at 0.01 mg/kg body weight ICG dose.
13. A method for imaging a tissue or organ in a subject, comprising: administering to a subject in need of imaging a suitable amount of the composition of claim 1, and obtaining an image of a tissue or organ of said subject.
14. The method of claim 13, wherein the amount of the composition equals an ICG dose of between about 0.01 mg/kg body weight to about 0.5 mg/kg body weight.
15. The method of claim 13, wherein said tissue or organ is selected from the group consisting of: Lymphatic vessels, Secondary lymphoid tissues, Blood vessels, Endothelial lesions, Tumors, Tertiary lymphoid tissues, Liver, Bile duct, Gall bladder, Intestine, Stomach, Brain, Breast, Lung, Heart, Eye, Ovarian, Prostate.
16. The method of claim 13, wherein the administration route for said composition is selected from the group consisting of systemic and local administrations.
17. The method of claim 16, wherein the systemic administration comprises intravascular injection.
18. The method of claim 16, wherein the local administration comprises subcutaneous injection, intradermal injection, submucous injection, subserous injection, intramuscular injection, oral administration, intranasal administration or intra- and peri-tumoral injection.
19. The method of claim 18, wherein the amount of the composition at single injection site equals an ICG dose between 0.1 ng and 0.1 mg.

* * * * *